US009737292B2

(12) United States Patent
Sullivan et al.

(10) Patent No.: US 9,737,292 B2
(45) Date of Patent: Aug. 22, 2017

(54) KNOTLESS SUTURE ANCHORS AND METHODS OF TISSUE REPAIR

(71) Applicant: Arthrex, Inc., Naples, FL (US)

(72) Inventors: Derek C. Sullivan, Bonita Springs, FL (US); Thomas Dooney, Jr., Naples, FL (US); Allen E. Holowecky, Naples, FL (US); Paul C. Brady, Knoxville, TN (US); Benjamin G. Domb, Chicago, IL (US)

(73) Assignee: Arthrex, Inc., Naples, FL (US)

( * ) Notice: Subject to any disclaimer, the term of this patent is extended or adjusted under 35 U.S.C. 154(b) by 852 days.

(21) Appl. No.: 13/916,104

(22) Filed: Jun. 12, 2013

(65) Prior Publication Data

US 2013/0345749 A1    Dec. 26, 2013

Related U.S. Application Data

(60) Provisional application No. 61/663,029, filed on Jun. 22, 2012.

(51) Int. Cl.
*A61B 17/04* (2006.01)
*A61B 17/88* (2006.01)

(52) U.S. Cl.
CPC ...... *A61B 17/0401* (2013.01); *A61B 17/0469* (2013.01); *A61B 17/0482* (2013.01);
(Continued)

(58) Field of Classification Search
CPC .......... A61B 17/0401; A61B 2017/044; A61B 2017/0458; A61B 2017/0459;
(Continued)

(56) References Cited

U.S. PATENT DOCUMENTS 3,176,316 A    4/1965   Bodell
4,187,558 A    2/1980   Dahlen et al.
(Continued)

FOREIGN PATENT DOCUMENTS

DE    299 10 202 U1    9/1999
DE    201 01 791 U1    6/2001
(Continued)

OTHER PUBLICATIONS

MaxFire MarXmen Meniscal Repair Surgical Technique, BIOMET Sports Medicine, Mar. 2009.
(Continued)

*Primary Examiner* — Richard Louis
(74) *Attorney, Agent, or Firm* — Blank Rome LLP

(57) ABSTRACT

Systems and methods for soft tissue to bone repairs employing tensionable knotless anchors, without knot tying. The tensionable knotless anchors may be used by themselves or in combination with additional constructs (which may have a similar or different configuration, i.e., modified according to the specific repair) and with the flexible strands provided through tissue, around tissue, or through and around tissue to be repaired or fixated. The tensionable knotless anchors may be used to achieve simple stitch repairs, mattress stitch repairs or interlocked looped mattress repairs, among others. The tensionable knotless anchors may be also provided in a daisy chain configuration, i.e., with the suture from one anchor passed through the eyelet/loop of the shuttle/pull device of another anchor and repeated in a pattern.

20 Claims, 33 Drawing Sheets

(52) U.S. Cl.
CPC ...... *A61B 17/0485* (2013.01); *A61B 17/8875* (2013.01); *A61B 2017/044* (2013.01); *A61B 2017/0409* (2013.01); *A61B 2017/0414* (2013.01); *A61B 2017/0427* (2013.01); *A61B 2017/0458* (2013.01); *A61B 2017/0459* (2013.01); *A61B 2017/0496* (2013.01)

(58) Field of Classification Search
CPC .... A61B 2017/0496; A61B 2017/0427; A61B 17/0482; A61B 17/0485; A61B 17/0469; A61B 17/8875; A61B 2017/0414; A61B 2017/0409
See application file for complete search history.

(56) References Cited

U.S. PATENT DOCUMENTS

| | | | |
|---|---|---|---|
| 4,301,551 A | 11/1981 | Dore et al. | |
| 4,400,833 A | 8/1983 | Kurland | |
| 4,776,851 A | 10/1988 | Bruchman et al. | |
| 4,790,850 A | 12/1988 | Dunn et al. | |
| 4,792,336 A | 12/1988 | Hlavacek et al. | |
| 4,851,005 A | 7/1989 | Hunt et al. | |
| 4,863,471 A | 9/1989 | Mansat | |
| 4,917,700 A | 4/1990 | Aikins | |
| 4,932,972 A | 6/1990 | Dunn et al. | |
| 5,024,669 A | 6/1991 | Peterson et al. | |
| 5,026,398 A | 6/1991 | May et al. | |
| 5,129,902 A | 7/1992 | Goble et al. | |
| 5,171,274 A | 12/1992 | Fluckiger et al. | |
| 5,211,647 A | 5/1993 | Schmieding | |
| 5,217,495 A | 6/1993 | Kaplan et al. | |
| 5,263,984 A | 11/1993 | Li et al. | |
| 5,266,075 A | 11/1993 | Clark et al. | |
| 5,306,301 A | 4/1994 | Graf et al. | |
| 5,320,626 A | 6/1994 | Schmieding | |
| 5,397,357 A | 3/1995 | Schmieding et al. | |
| 5,562,669 A | 10/1996 | McGuire | |
| 5,562,683 A * | 10/1996 | Chan | A61B 17/0469 289/17 |
| 5,575,819 A | 11/1996 | Amis | |
| 5,628,756 A | 5/1997 | Barker, Jr. et al. | |
| 5,643,266 A | 7/1997 | Li | |
| 5,645,588 A | 7/1997 | Graf et al. | |
| 5,658,313 A * | 8/1997 | Thal | A61B 17/0401 24/357 |
| 5,931,869 A | 8/1999 | Boucher et al. | |
| 5,961,520 A | 10/1999 | Beck, Jr. et al. | |
| 5,964,764 A | 10/1999 | West, Jr. et al. | |
| 6,056,752 A | 5/2000 | Roger | |
| 6,099,530 A | 8/2000 | Simonian et al. | |
| 6,099,568 A | 8/2000 | Simonian et al. | |
| 6,110,207 A | 8/2000 | Eichhorn et al. | |
| 6,159,234 A | 12/2000 | Bonutti et al. | |
| 6,193,754 B1 | 2/2001 | Seedhom | |
| 6,203,572 B1 | 3/2001 | Johnson et al. | |
| 6,283,996 B1 | 9/2001 | Chervitz et al. | |
| 6,296,659 B1 | 10/2001 | Foerster | |
| 6,325,804 B1 | 12/2001 | Wenstrom, Jr. et al. | |
| 6,517,578 B2 | 2/2003 | Hein | |
| 6,533,802 B2 | 3/2003 | Bojarski et al. | |
| 7,097,654 B1 | 8/2006 | Freedland | |
| 7,494,506 B2 | 2/2009 | Brulez et al. | |
| 7,686,838 B2 | 3/2010 | Wolf et al. | |
| 7,749,250 B2 | 7/2010 | Stone et al. | |
| 7,776,039 B2 | 8/2010 | Bernstein et al. | |
| 7,819,898 B2 | 10/2010 | Stone et al. | |
| 7,828,855 B2 | 11/2010 | Ellis et al. | |
| 7,875,057 B2 | 1/2011 | Cook et al. | |
| 7,905,903 B2 | 3/2011 | Stone et al. | |
| 7,914,539 B2 | 3/2011 | Stone et al. | |
| 8,109,965 B2 | 2/2012 | Stone et al. | |
| 8,118,836 B2 | 2/2012 | Denham et al. | |
| 8,162,997 B2 | 4/2012 | Struhl | |
| 8,206,446 B1 | 6/2012 | Montgomery | |
| 8,231,654 B2 | 7/2012 | Kaiser et al. | |
| 2001/0041938 A1 | 11/2001 | Hein | |
| 2002/0161439 A1 | 10/2002 | Strobel et al. | |
| 2003/0114929 A1 | 6/2003 | Knudsen et al. | |
| 2004/0015171 A1 | 1/2004 | Bojarski et al. | |
| 2004/0059415 A1 | 3/2004 | Schmieding | |
| 2004/0073306 A1 | 4/2004 | Eichhorn et al. | |
| 2004/0243235 A1 | 12/2004 | Goh et al. | |
| 2004/0267360 A1 | 12/2004 | Huber | |
| 2005/0004670 A1 | 1/2005 | Gebhardt et al. | |
| 2005/0033363 A1 * | 2/2005 | Bojarski | A61B 17/0401 606/228 |
| 2005/0065533 A1 | 3/2005 | Magen et al. | |
| 2005/0070906 A1 | 3/2005 | Clark et al. | |
| 2005/0137704 A1 | 6/2005 | Steenlage | |
| 2005/0149187 A1 | 7/2005 | Clark et al. | |
| 2005/0171603 A1 | 8/2005 | Justin et al. | |
| 2005/0203623 A1 | 9/2005 | Steiner et al. | |
| 2005/0261766 A1 | 11/2005 | Chervitz et al. | |
| 2006/0004364 A1 | 1/2006 | Green et al. | |
| 2006/0067971 A1 | 3/2006 | Story et al. | |
| 2006/0095130 A1 | 5/2006 | Caborn et al. | |
| 2006/0106423 A1 * | 5/2006 | Weisel | A61B 17/0401 606/232 |
| 2006/0122608 A1 * | 6/2006 | Fallin | A61B 17/0401 606/232 |
| 2006/0142769 A1 | 6/2006 | Collette | |
| 2006/0161159 A1 * | 7/2006 | Dreyfuss | A61B 17/0401 606/232 |
| 2006/0265064 A1 | 11/2006 | Re et al. | |
| 2007/0021839 A1 | 1/2007 | Lowe | |
| 2007/0083236 A1 | 4/2007 | Sikora et al. | |
| 2007/0118217 A1 | 5/2007 | Brulez et al. | |
| 2007/0162123 A1 | 7/2007 | Whittaker et al. | |
| 2007/0162125 A1 | 7/2007 | LeBeau et al. | |
| 2007/0179531 A1 | 8/2007 | Thornes | |
| 2007/0225805 A1 | 9/2007 | Schmieding | |
| 2007/0239209 A1 | 10/2007 | Fallman | |
| 2007/0239275 A1 | 10/2007 | Willobee | |
| 2007/0250163 A1 | 10/2007 | Cassani | |
| 2007/0270857 A1 | 11/2007 | Lombardo et al. | |
| 2008/0046009 A1 | 2/2008 | Albertorio et al. | |
| 2008/0065114 A1 * | 3/2008 | Stone | A61B 17/0401 606/139 |
| 2008/0177302 A1 | 7/2008 | Shurnas | |
| 2008/0188935 A1 | 8/2008 | Saylor et al. | |
| 2008/0188936 A1 | 8/2008 | Ball et al. | |
| 2008/0208252 A1 | 8/2008 | Holmes | |
| 2008/0215150 A1 | 9/2008 | Koob et al. | |
| 2008/0228271 A1 | 9/2008 | Stone et al. | |
| 2008/0234819 A1 | 9/2008 | Schmieding et al. | |
| 2008/0243248 A1 | 10/2008 | Stone et al. | |
| 2008/0255613 A1 * | 10/2008 | Kaiser | A61B 17/0401 606/232 |
| 2008/0275553 A1 | 11/2008 | Wolf et al. | |
| 2008/0275554 A1 | 11/2008 | Iannarone et al. | |
| 2008/0300683 A1 | 12/2008 | Altman et al. | |
| 2008/0312689 A1 | 12/2008 | Denham et al. | |
| 2009/0018654 A1 | 1/2009 | Schmieding et al. | |
| 2009/0030516 A1 | 1/2009 | Imbert | |
| 2009/0054982 A1 | 2/2009 | Cimino | |
| 2009/0062854 A1 | 3/2009 | Kaiser et al. | |
| 2009/0082805 A1 * | 3/2009 | Kaiser | A61B 17/0401 606/228 |
| 2009/0187244 A1 | 7/2009 | Dross | |
| 2009/0216326 A1 | 8/2009 | Hirpara et al. | |
| 2009/0228017 A1 | 9/2009 | Collins | |
| 2009/0234451 A1 | 9/2009 | Manderson | |
| 2009/0265003 A1 | 10/2009 | Re et al. | |
| 2009/0275950 A1 | 11/2009 | Sterrett et al. | |
| 2009/0306776 A1 | 12/2009 | Murray | |
| 2009/0306784 A1 | 12/2009 | Blum | |
| 2009/0312776 A1 | 12/2009 | Kaiser et al. | |
| 2010/0049258 A1 | 2/2010 | Dougherty | |
| 2010/0049319 A1 | 2/2010 | Dougherty | |
| 2010/0063541 A1 * | 3/2010 | Brunelle | A61B 17/0401 606/232 |
| 2010/0100182 A1 | 4/2010 | Barnes et al. | |

(56) References Cited

U.S. PATENT DOCUMENTS

| | | |
|---|---|---|
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0208239 A1* | 8/2011 | Stone .................. A61B 17/0469 606/228 |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |
| 2013/0165972 A1 | 6/2013 | Sullivan |

FOREIGN PATENT DOCUMENTS

| | | |
|---|---|---|
| EP | 0 440 991 A1 | 8/1991 |
| EP | 1 108 401 A1 | 6/2001 |
| EP | 1 707 127 A1 | 10/2006 |
| WO | WO 2007/002561 A1 | 1/2007 |
| WO | WO 2008/091690 A1 | 7/2008 |

OTHER PUBLICATIONS

ToggleLoc Femoral Fixation for ACL Reconstruction, BIOMET Sports Medicine, 2008.

* cited by examiner

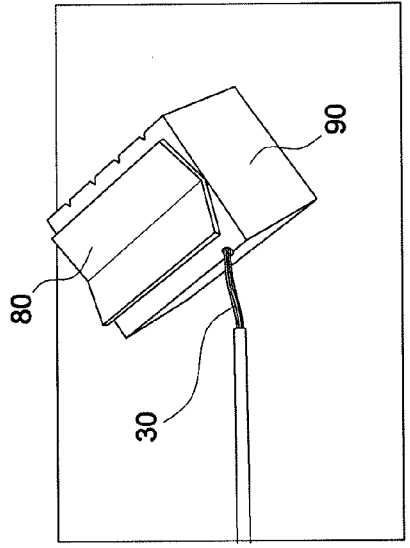
FIG. 3
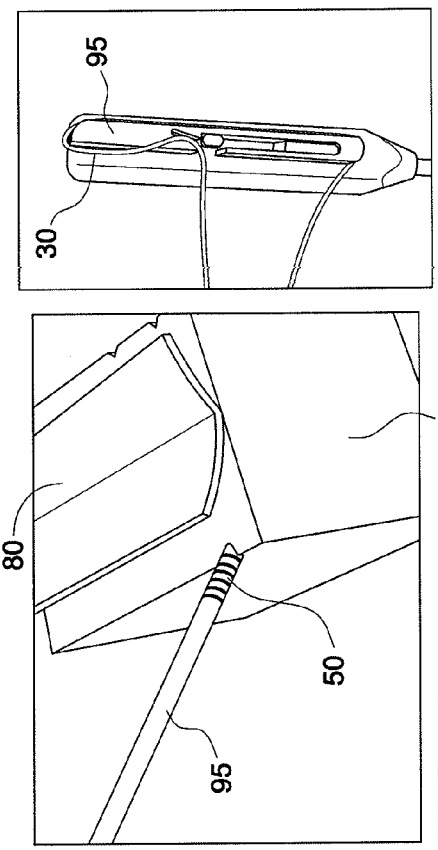
FIG. 1
FIG. 2
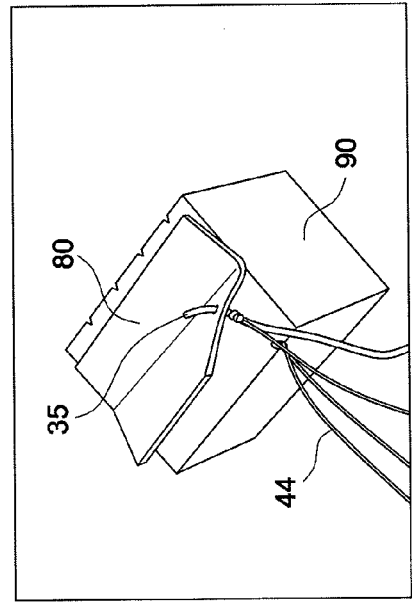
FIG. 5
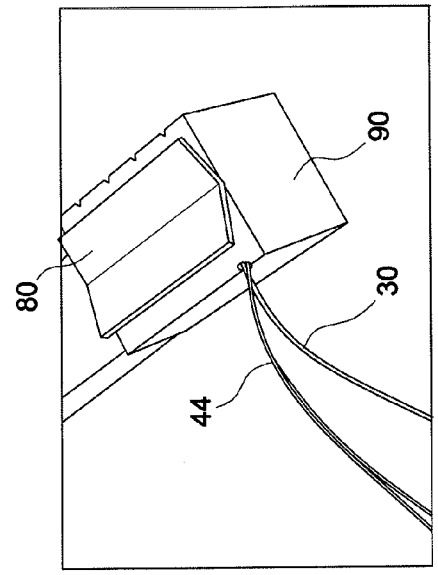
FIG. 4

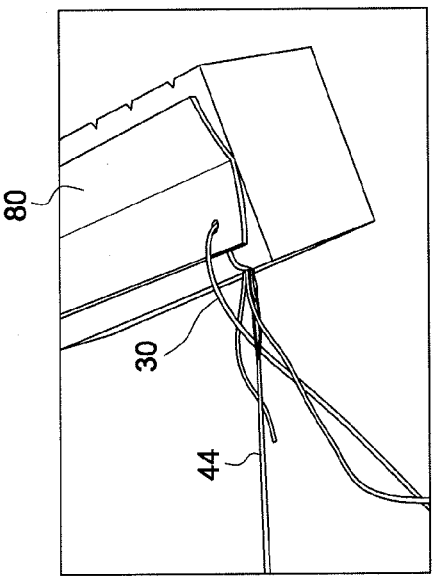
FIG. 11
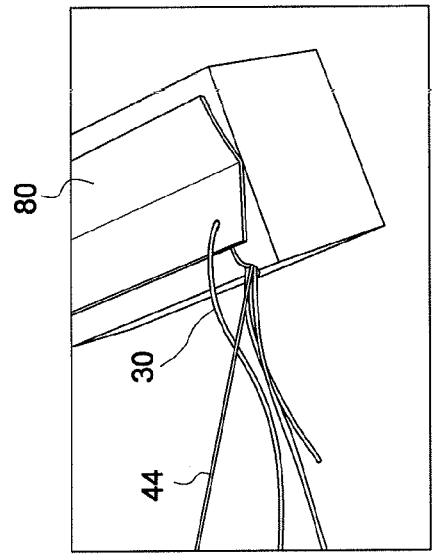
FIG. 10
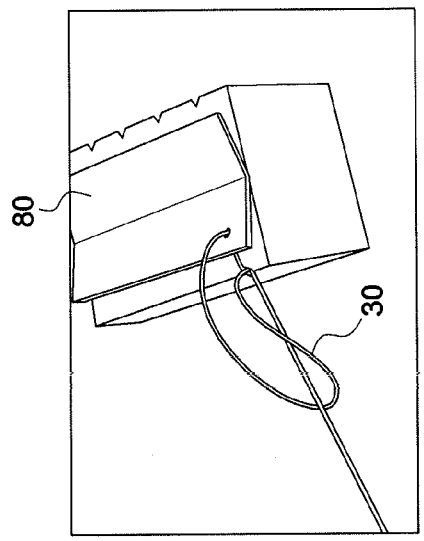
FIG. 13
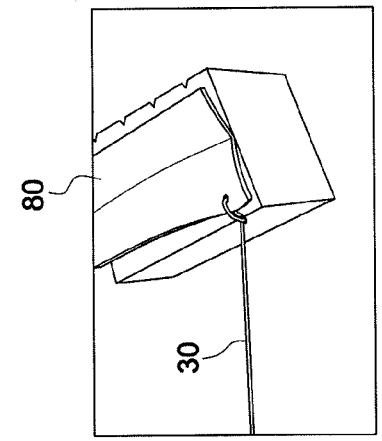
FIG. 14
FIG. 12

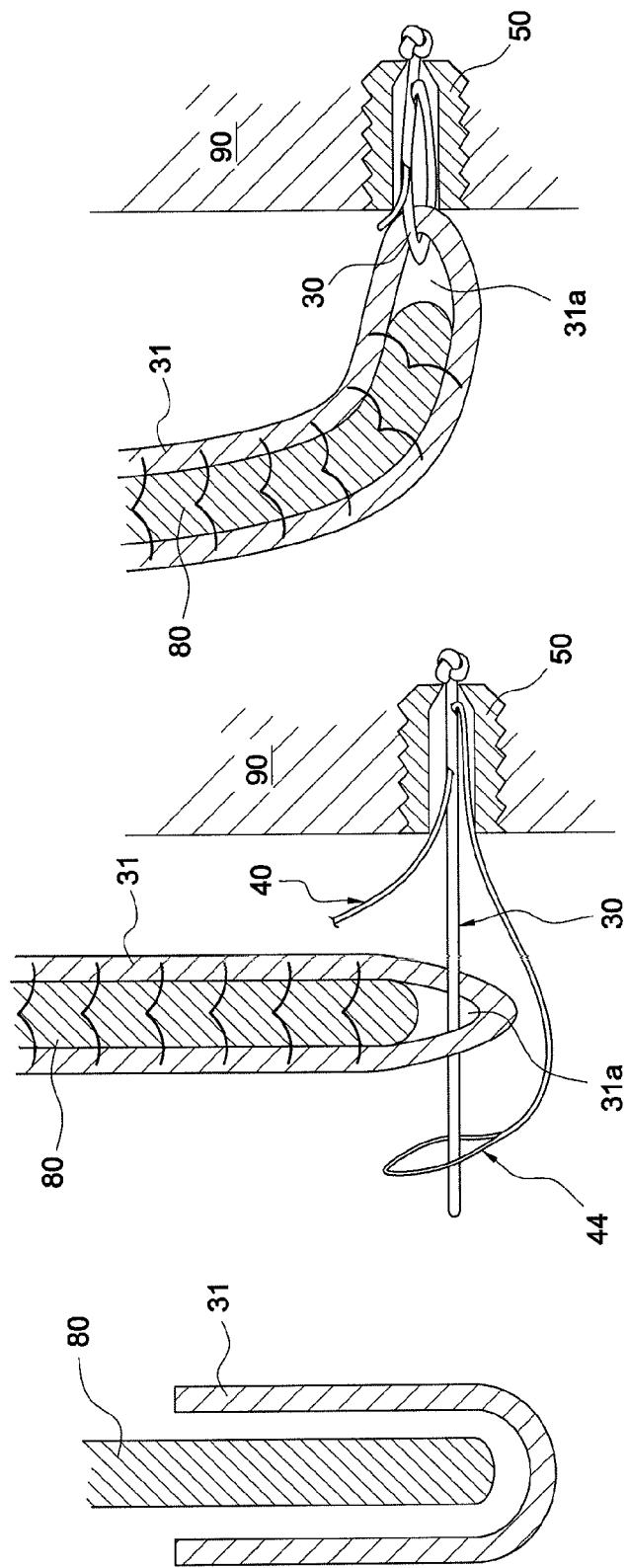

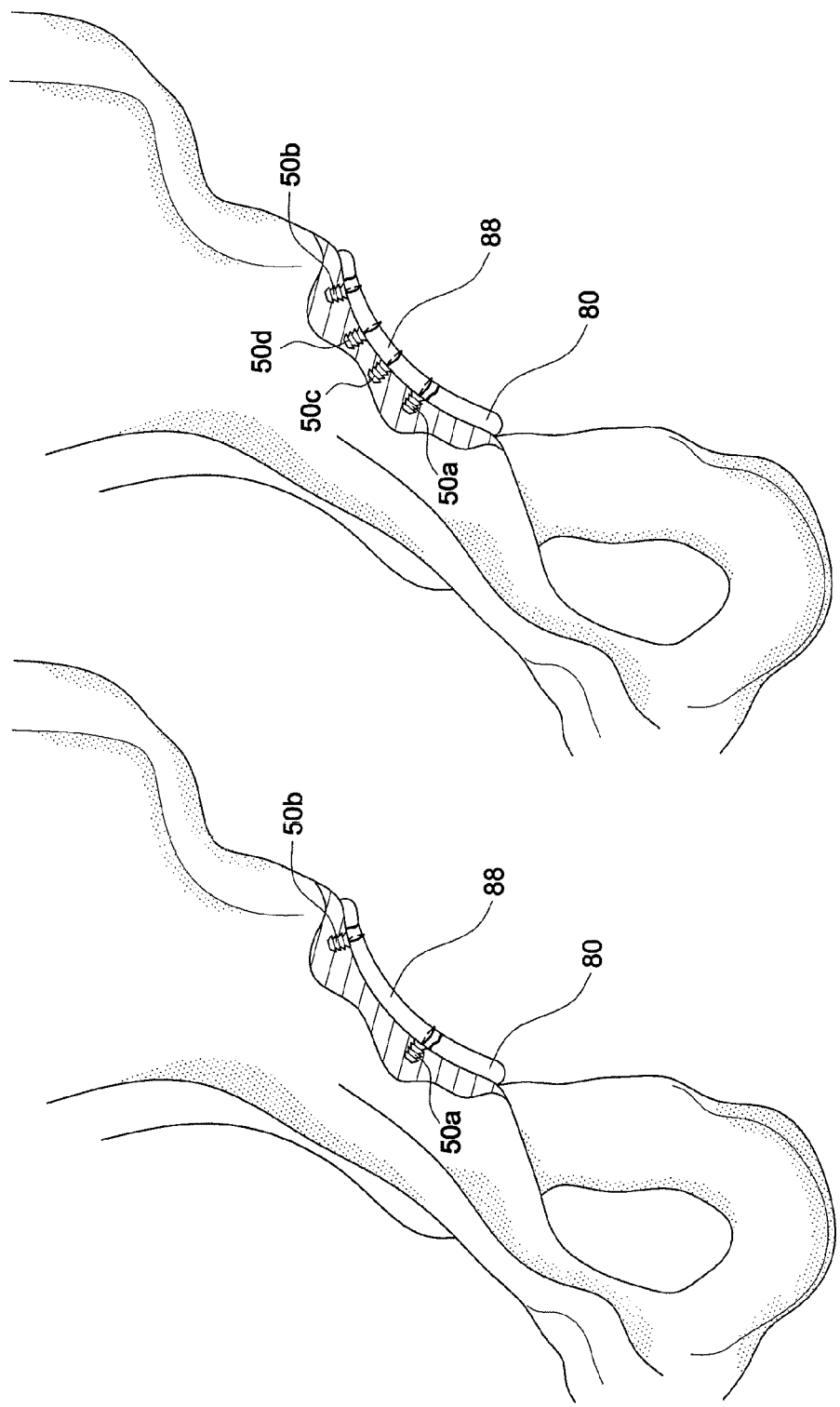

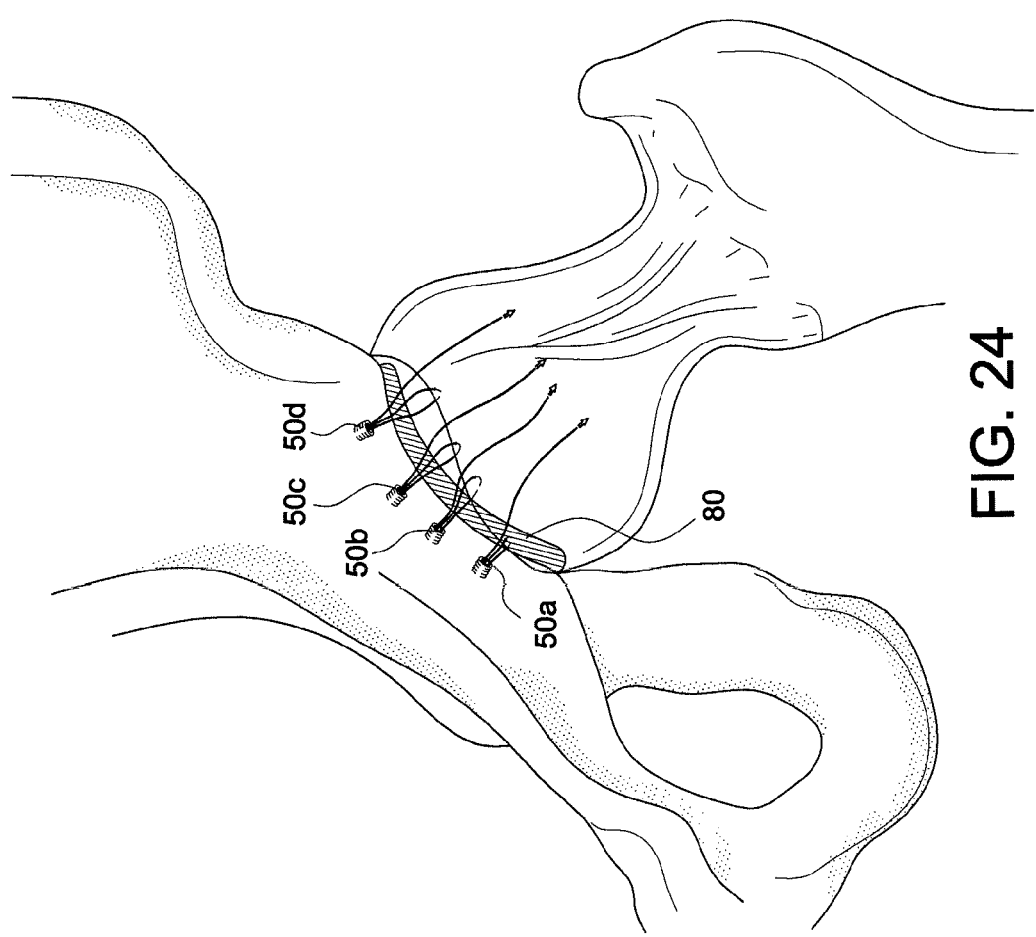

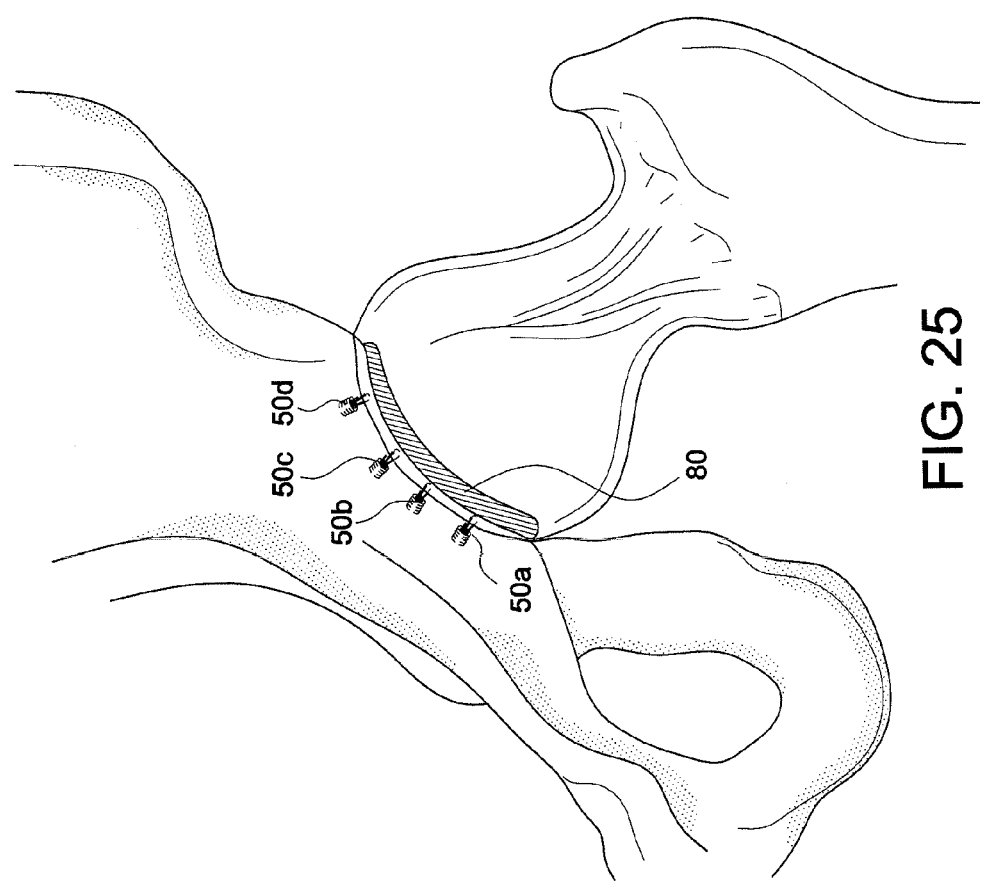

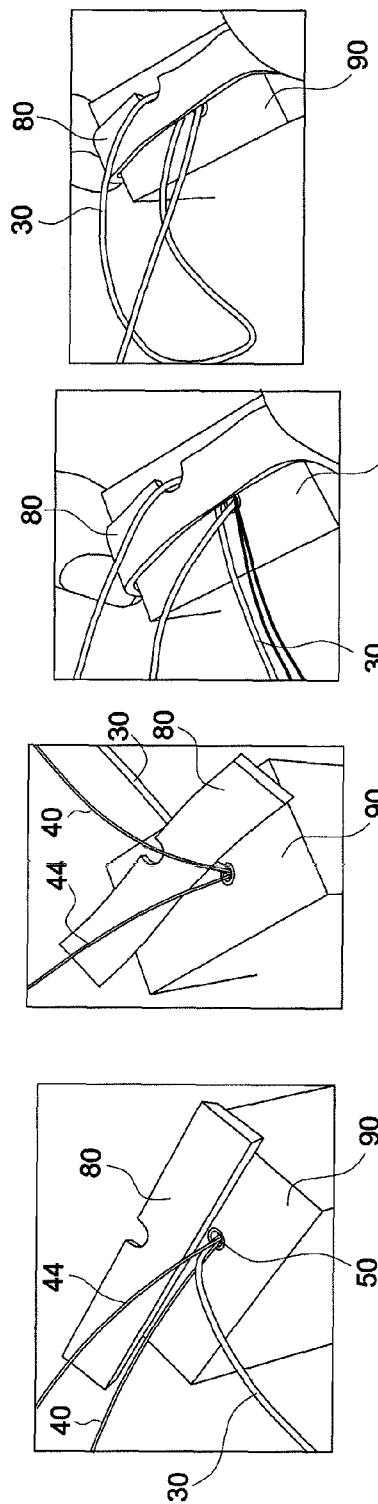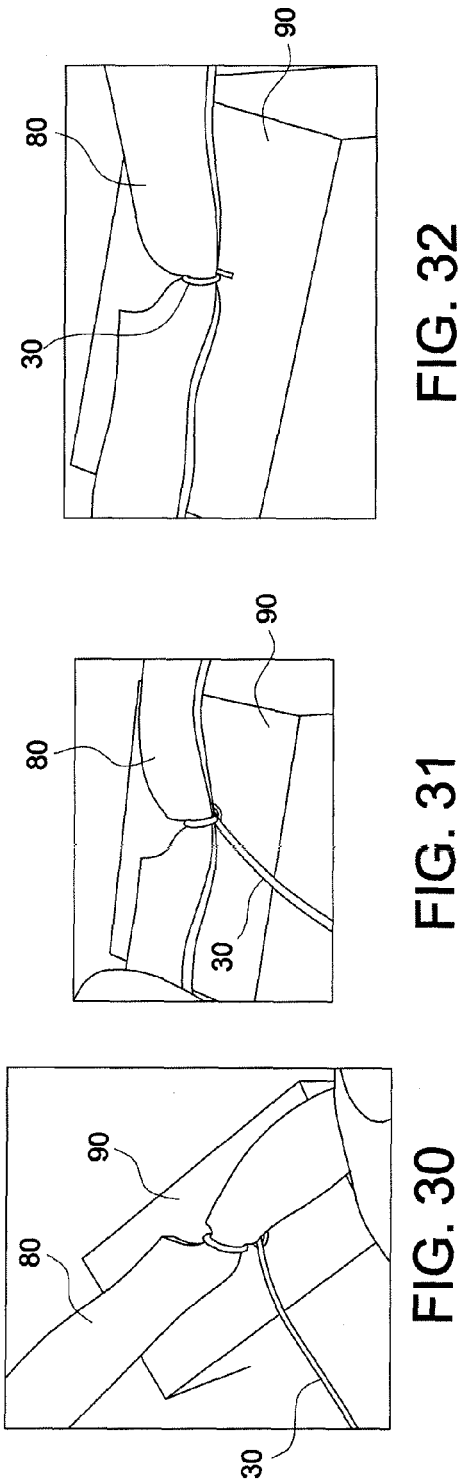

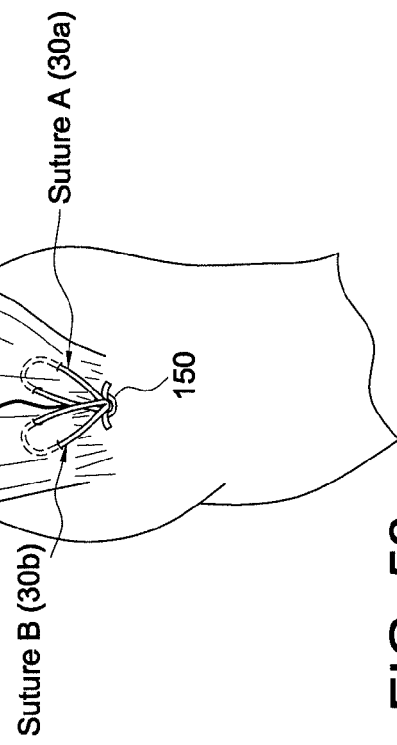
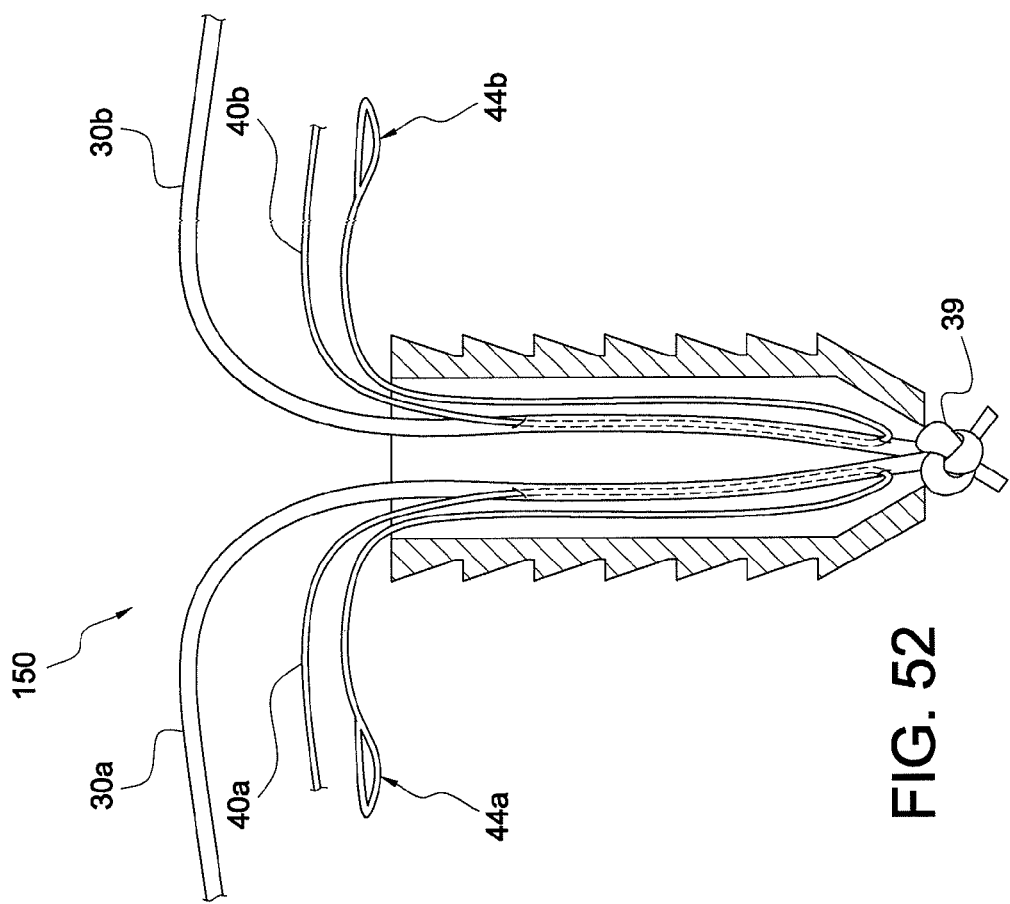
FIG. 52
FIG. 53

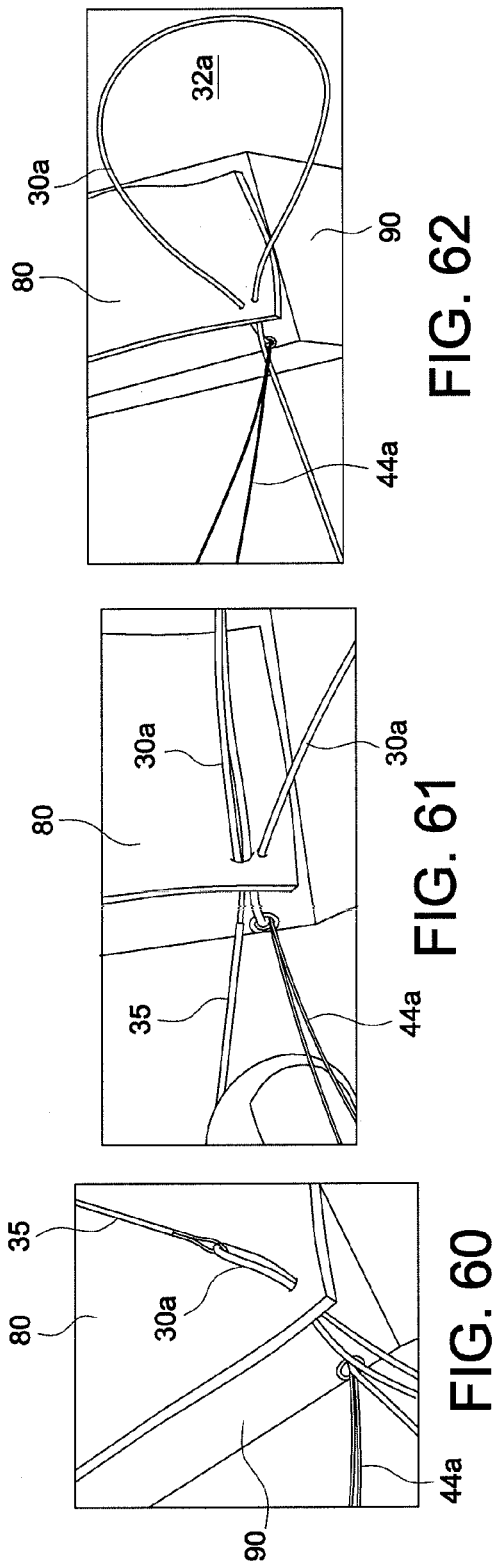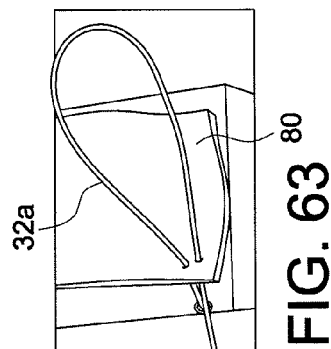

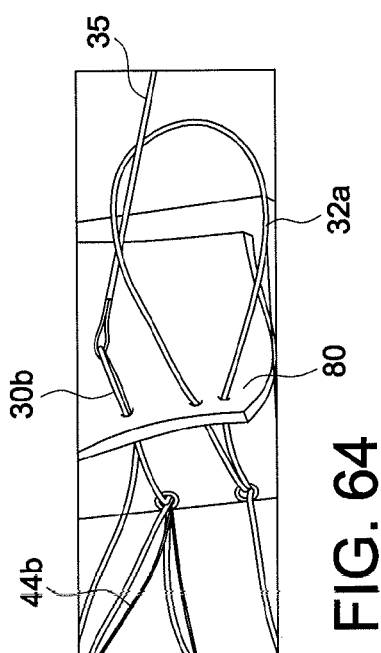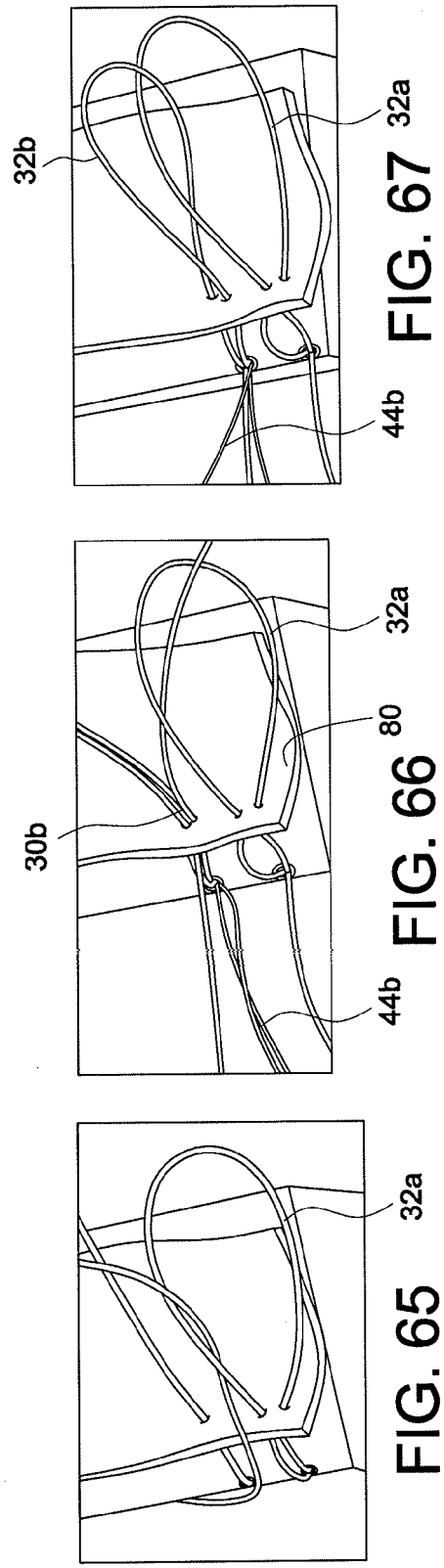

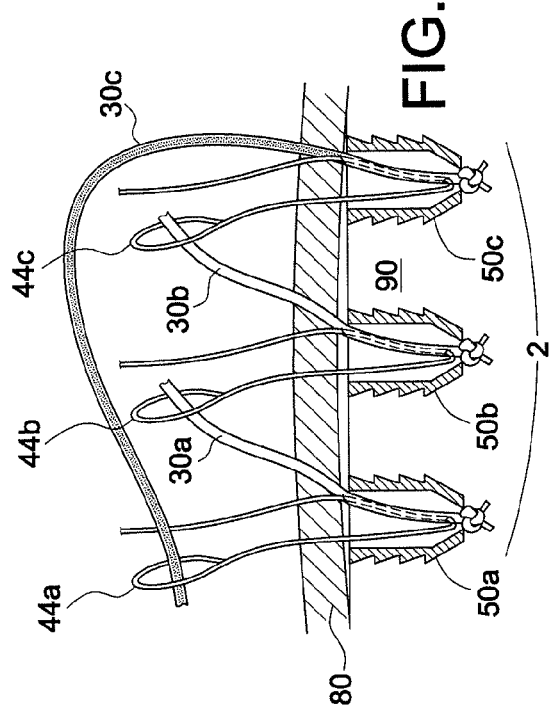
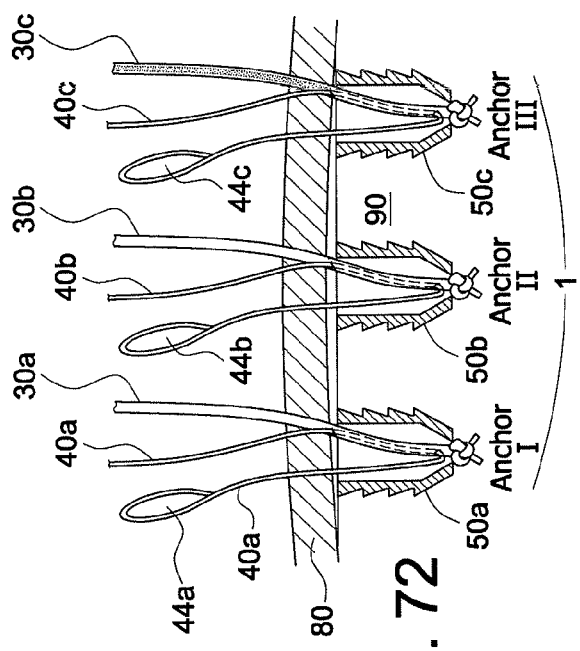
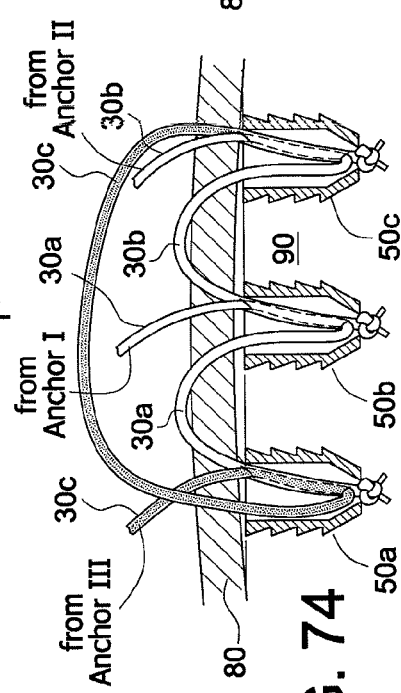
FIG. 72
FIG. 73
FIG. 74
FIG. 75

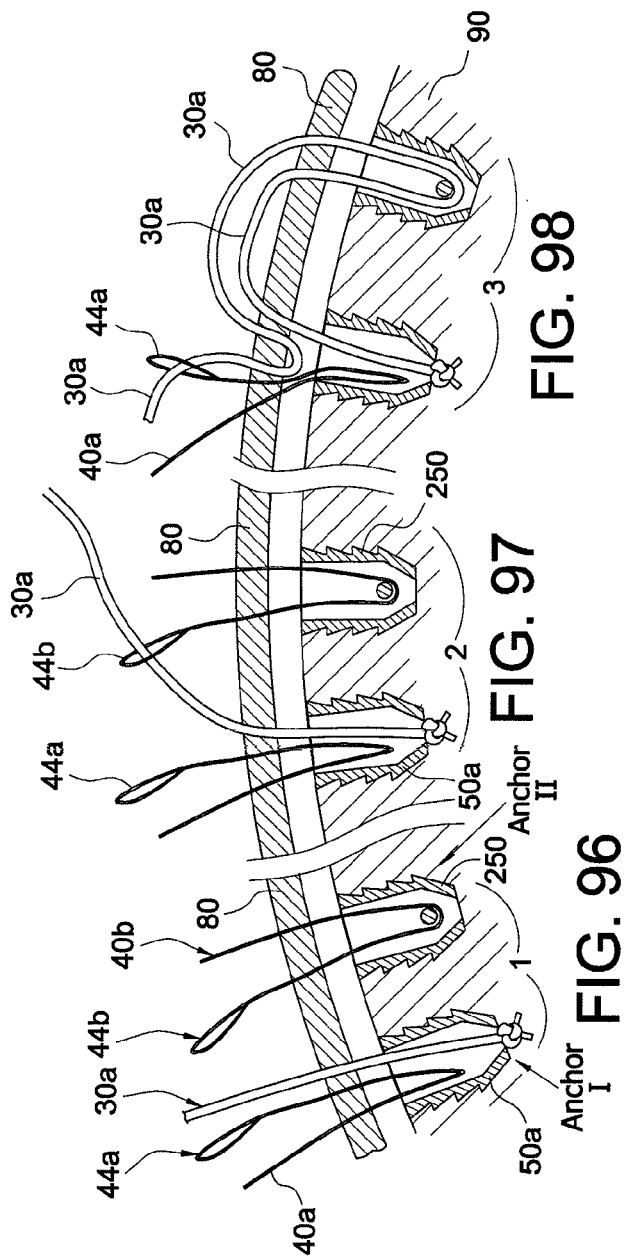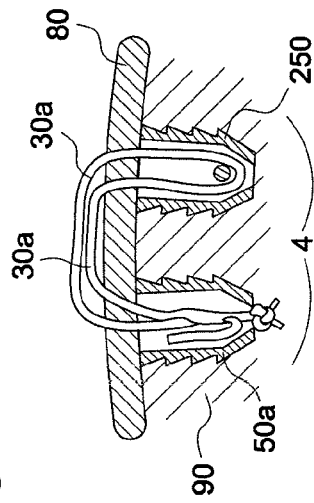

KNOTLESS SUTURE ANCHORS AND METHODS OF TISSUE REPAIR

CROSS-REFERENCE TO RELATED APPLICATIONS

This application claims the benefit of U.S. Provisional Application No. 61/663,029 filed Jun. 22, 2012, the disclosure of which is incorporated by reference in its entirety herein.

FIELD OF THE INVENTION

The present invention relates to surgical devices and, in particular, to knotless suture constructs and associated methods of tissue repairs.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

There is a need for knotless suture anchor constructs with improved design that allow tensioning of the tissue after implantation of the suture anchors. Also needed are improved technologies for knotless fixation of soft tissue with easier suture management and increased tensioning of the tissue.

SUMMARY OF THE INVENTION

The present invention fulfills the above needs and objectives by providing knotless, tensionable suture anchors and methods of tissue repair employing one or more of such knotless, tensionable suture anchors. The suture anchors of the present invention allow for tensioning after insertion in bone (to allow attached tissue to be brought proximate to bone) and do not require tying of any knots.

Other features and advantages of the present invention will become apparent from the following description of the invention.

BRIEF DESCRIPTION OF THE DRAWINGS

FIGS. 1-14 illustrate subsequent steps of a method of tissue repair (simple stitch of soft tissue) using a tensionable knotless anchor according to an exemplary embodiment of the present invention.

FIGS. 15-17 illustrate subsequent steps of a method of tissue repair (tendon repair) using a tensionable knotless anchor according to an exemplary embodiment of the present invention.

FIGS. 18-21 illustrate subsequent steps of a method of tissue repair (hip labral repair) using multiple tensionable knotless anchors according to an exemplary embodiment of the present invention.

FIGS. 22-25 illustrate subsequent steps of a method of tissue repair (hip capsular repair) using multiple tensionable knotless anchors according to an exemplary embodiment of the present invention.

FIGS. 26-32 illustrate subsequent steps of a method of tissue repair (simple stitch repair) using a tensionable knotless anchor according to an exemplary embodiment of the present invention.

FIGS. 52 and 53 illustrate subsequent steps of a method of tissue repair (modified anchor rotator cuff repair) using a modified tensionable knotless anchor according to an exemplary embodiment of the present invention.

FIGS. 60-71 illustrate subsequent steps of a method of tissue repair (interlocked looped mattress over two anchors repair) using multiple interconnected tensionable knotless anchors (with interlocked loops) according to an exemplary embodiment of the present invention.

FIGS. 72-75 illustrate subsequent steps of a method of tissue repair (two or more anchors in daisy chain) using multiple interconnected tensionable knotless anchors according to an exemplary embodiment of the present invention.

FIGS. 96-99 illustrate subsequent steps of a method of tissue repair (simple two anchor mattress repair) using two different tensionable knotless anchors together (the anchors having different configurations) according to an exemplary embodiment of the present invention.

DETAILED DESCRIPTION OF THE EMBODIMENTS

Figure 7:
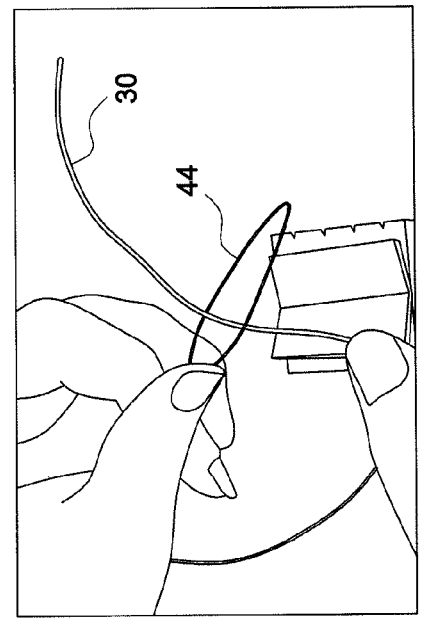
Figure 9:
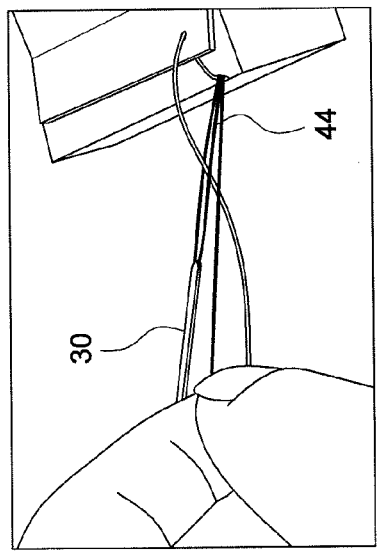

The present invention provides surgical constructs, systems and techniques for knotless soft tissue repair and fixation, such as fixation of soft tissue (ligament, tendon, graft, etc.) to bone. The knotless anchor constructs may be employed for any soft tissue repair including labral, rotator cuff, Achilles tendon, biceps and hip repairs, among many others.

The knotless suture constructs of the present invention use a mechanism similar to that of knotless SutureTak® but provide improvements in the design of the anchor constructs (for example, an anchor with two separate flexible strands or an anchor without a flexible strand but with one or more suture shuttle devices) as well as in the suture management and tensioning.

The surgical constructs and systems detailed below comprise fixation devices (tensionable knotless anchors) having various configurations that are inserted into bone with a flexible strand (for example, a suture) provided within the fixation device and optionally a shuttle/pull device (a suture passing instrument) attached to the flexible strand. The flexible strand and the shuttle/pull device attached to it allow the formation of a splice within the body of the anchor and during the tissue repair procedure to finalize the construct. The shuttle/pull device is provided within the strand (inside of the strand) and forms the splice subsequent to the insertion of the fixation device within the bone (and subsequent to attachment to soft tissue to be repaired or fixated) to allow formation of the final fixation device with a knotless self-locking mechanism that allows the user (for example, the surgeon) to control the tension of the strand on the soft tissue to be attached to bone.

Details of the formation of an exemplary knotless suture anchor employed in the embodiments of the present invention and with the splice-forming mechanism detailed above are set forth in U.S. Patent Application Publication No. 2013/0096611, entitled "Tensionable Knotless Anchors with Splice and Methods of Tissue Repair" and U.S. application Ser. No. 13/709,138 filed Dec. 10, 2012, entitled "Tensionable Knotless Anchor Systems and Methods of Tissue Repair," the disclosures of both of which are incorporated in their entirety herewith.

The present invention also provides methods of soft tissue repair which do not require tying of knots and allow adjustment of both the tension of the suture and the location of the tissue with respect to the bone. In the exemplary methods detailed below with reference to FIGS. 1-101, the tensionable knotless anchors may be used by themselves or in combination with additional constructs (which may have a similar or different configuration, i.e., modified according to the specific repair) and with the flexible strand provided through tissue, around tissue, or through and around tissue to be repaired or fixated. The tensionable knotless anchors may be used to achieve simple stitch repairs, mattress stitch repairs or interlocked looped mattress repairs, among others. The tensionable knotless anchors may be also provided in a daisy chain configuration, i.e., with the suture from one anchor passed through the eyelet/loop of the shuttle/pull device of another anchor and repeated in a pattern (to allow the formation of a splice within each anchor with a shuttle/pull device of another anchor).

The methods and constructs of the present invention will be detailed below with reference to an exemplary knotless suture anchor 50, 50a-50d (or anchors having a configuration similar to it such as anchors 150, 250). Details of an anchor similar to knotless suture anchor 50 are set forth in U.S. Application Publication No. 2013/0096611, entitled "Tensionable Knotless Anchors with Splice and Methods of Tissue Repair "(the disclosure of which is incorporated in its entirety herewith), but are also provided in this application (for ease of understanding of the embodiments below), and with reference to FIGS. 102 and 103.

Figure 102:
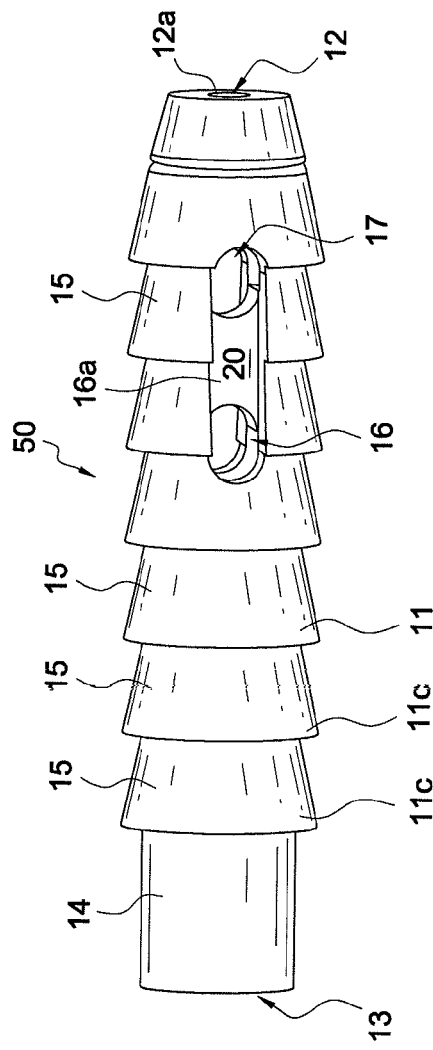
FIGS. 102 and 103 illustrate a side view and a cross-sectional view, respectively, of a tensionable knotless anchor employed in the exemplary methods of tissue repair and fixation according to the present invention.
Figure 103:
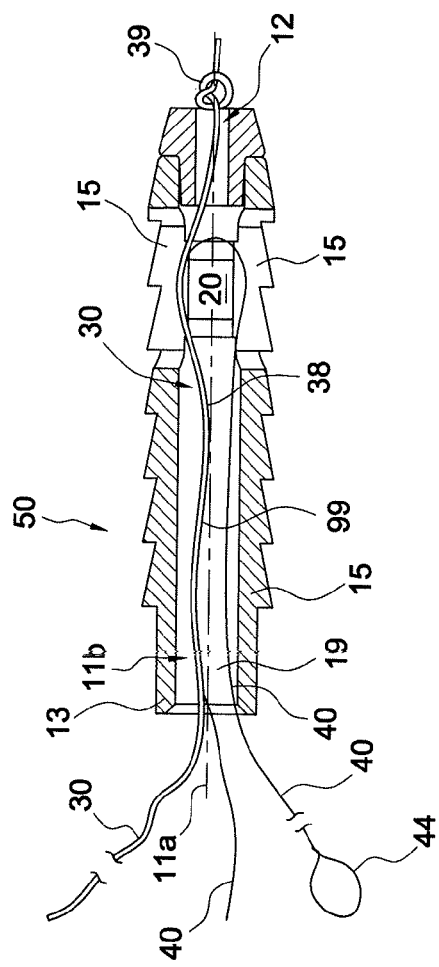

The tensionable knotless anchor 50 shown in FIGS. 102 and 103 has an anchor body 11 provided with a longitudinal axis 11a, a proximal end 13 and a distal end 12, and a plurality of ribs 15 extending circumferentially around it. Openings/channels 16 and 17 allow threading suture(s) and/or suture passing device(s) around post 20, as detailed below. Cannulation 11b extends along the body 11 to allow passage of flexible strands and of suture passing devices, as detailed below. Cylindrical portion 14 is provided at the proximal end 13 of the anchor 50 and contains a socket 19 (FIG. 103) configured to securely engage a tip of a driver. Openings/channels 16, 17 are positioned opposite to each other relative to the post 20 and also symmetrically located relative to the post 20, to allow flexible strand 30 (suture 30) and shuttle/pull device 40 (suture passing instrument 40 or shuttle 40) provided with eyelet or loop 44 to pass and slide threthrough.

Tensionable knotless anchor 50 is loaded with tensionable construct 99 formed of suture 30 attached to the shuttle/pull device 40. To assembly anchor 50, suture 30, which is typically braided or multi-filament, is preloaded onto the anchor by tying static knot 39, which prevents suture 30 from passing through distal blind hole 12a. The suture may also be preloaded by insert molding or by any other means known in the art. Suture 30 passes around post 20, which is large enough to allow suture 30 to take gradual turns instead of sharp turns. Suture 30 then passes through cannulation 11b and proximal blind hole 13a. Tensionable knotless anchor 50 is loaded onto a driver (not shown in FIGS. 102 and 103), and suture 30 is tied to the driver (for example, wrapped around a cleft of the driver) to fasten tensionable knotless anchor 50 securely to the driver.

Prior to the fastening of the anchor 50 to the driver, suture passing device 40 (for example, a FiberLink ™or a nitinol loop) is threaded through suture 30 (i.e., attached to the suture 30 through splice region 38), as shown in FIG. 103. Suture passing device 40 includes an eyelet/loop 44 for passing suture and, optionally, a pull-ring (not shown). Suture passing device 40 passes through an aperture of suture 30, located either proximal or distal to distal blind hole 12a. It then exits an aperture of suture 30, within the tensionable knotless anchor 50, traverses around post 20, and through proximal blind hole 13a. Tensionable knotless anchor 50 loaded with tensionable construct 99 (formed of suture 30 attached to the suture passing device 40) is then secured into bone (for example, into a hole/socket/tunnel formed in the bone) by using the driver. Suture 30 is then passed through or around the tissue which is to be reattached to bone. Suture 30 is subsequently passed through eyelet/loop 44 of the suture passing device 40. Suture passing device 40 is then pulled, thereby pulling suture 30 towards tensionable knotless anchor 50 so that it doubles on itself inside the body of the tensionable knotless anchor. The suture passing device 40 has also been further pulled through the splice region 38 of suture 30, to form a splice within the strand 30 and within the body of the anchor 50.

Anchor 50 may be a screw-in anchor or a push-in style anchor. Anchor 50 may be formed of metal, biocompatible plastic such as PEEK or a bioabsorbable PLLA material. Socket 19 at the distal end 13 of the anchor 50 is configured to securely engage a tip of a driver, as detailed below. The socket of the anchor 50 may have any shape adapted to receive a driver tip for tapping or screw-in style anchors. Tensionable knotless anchor 50 may be made of one or more pieces, or may be provided as an integrated device. As detailed below, the tensionable knotless anchor 50 may be modified to carry more than one suture/shuttle construct (i.e., more than a flexible strand 30 and a shuttle/pull device 40), or may be modified to carry no suture but only one or more shuttle/pull devices, etc.

Figures 100, 101:
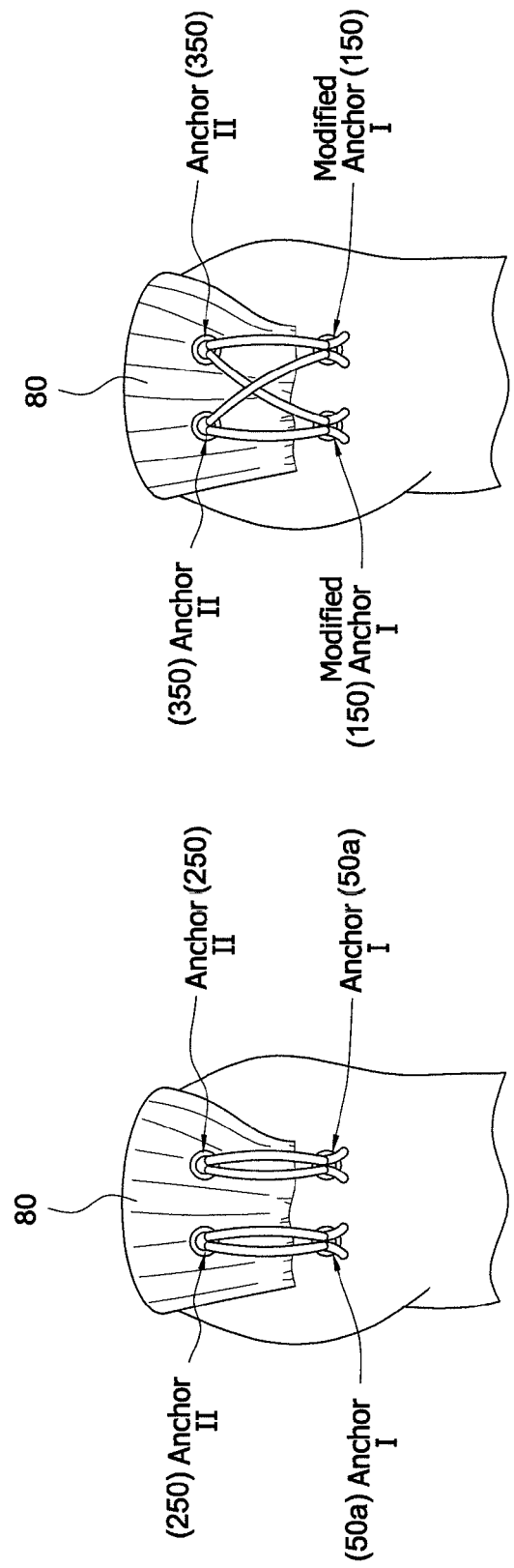
FIGS. 100 and 101 illustrate a tissue repair (rotator cuff repair using two anchors for medial row and two different anchors for lateral row) using two different-style tensionable knotless anchors together according to an exemplary embodiment of the present invention.

Reference is now made to FIGS. 1-101 which illustrate various suture anchor constructs and methods of attaching soft tissue to other tissue such as bone with such constructs. For simplicity, the suture anchor constructs have been grouped into three categories A-C, or three Embodiments A-C, set forth below.

Embodiment A—Single Anchor Constructs

The following description is a summary of the various methods of using the knotless anchor:

FIGS. 1-14

Figure 6:
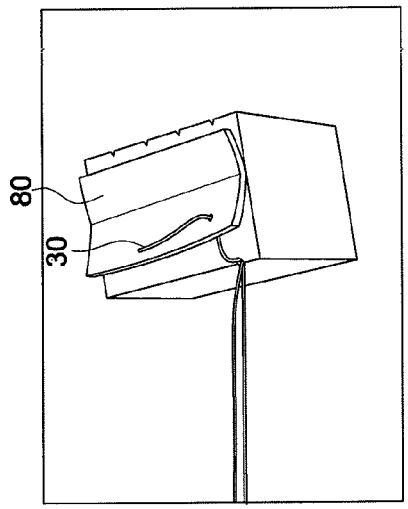
Figure 8:
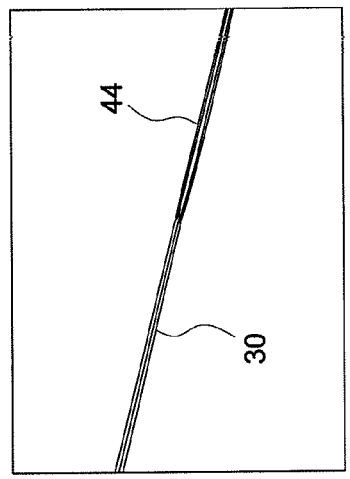

1) Simple Stitch Using Single Anchor to Attach Tissue for all Soft Tissue Repairs
   a. Insert anchor 50 into bone 90 using driver 95, remove driver 95 exposing suture 30 and suture shuttle 40 (with wire loop 44) (FIGS. 1-4)
      i. Can pre-drill bone hole 91 or tap
      ii. Can go through tissue 80 or under it directly into bone 90
   b. Pass suture 30 through tissue 80 using suture passing instrument 35 (FIGS. 5 and 6)
   c. Feed suture 30 through loop 44 of suture shuttle 40 (FIG. 7)
   d. Pull end of suture shuttle 40 to pull suture 30 through itself and the body of anchor 50 and create splice within the body of the anchor 50 (FIGS. 8-11)
   e. Pull suture 30 until desired tension and tissue position is reached (FIGS. 12-14)
   f. Cut suture 30 when repair is complete

FIGS. 15-17

Technique for Tendon Repair
   a. Whipstitch suture tape 31 (for example, FiberTape® 31) on tendon 80
   b. Create loop 31*a* at end of tendon 80 with FiberTape® 31
   c. Pass end of suture 30 from knotless anchor 50 through loop 31*a* at end of tendon 80
   d. Feed through loop 44 of suture shuttle 40 and complete steps d-f

FIGS. 18-21

Figure 18:
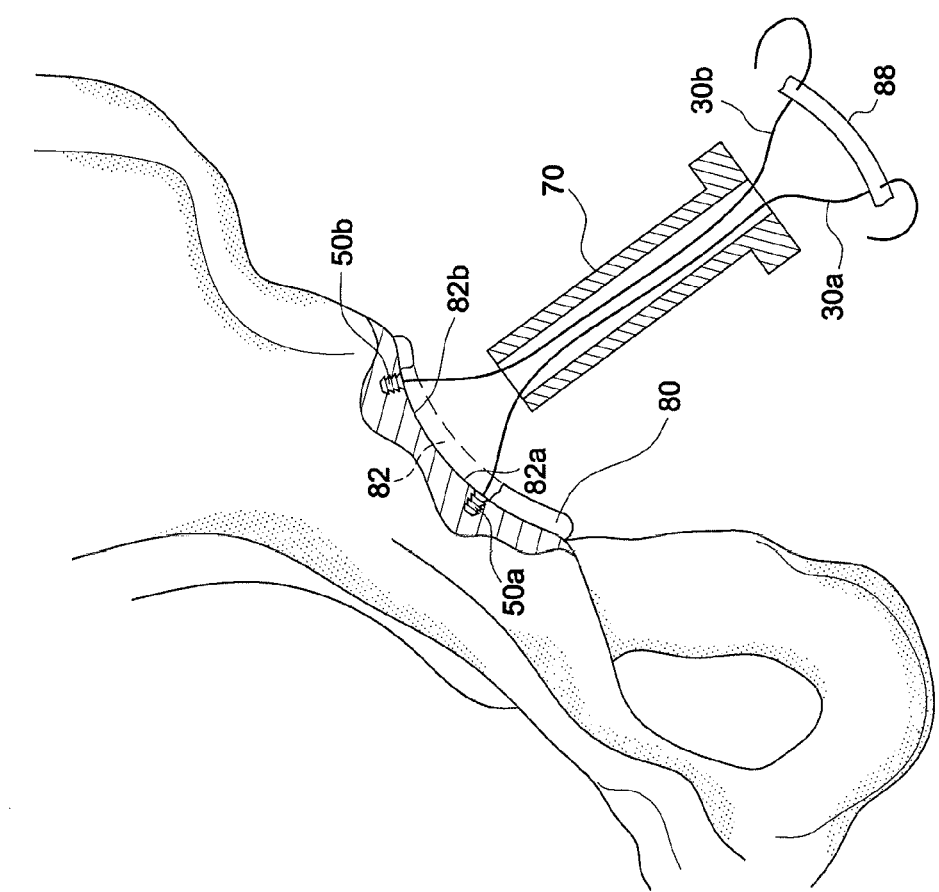
Figure 19:
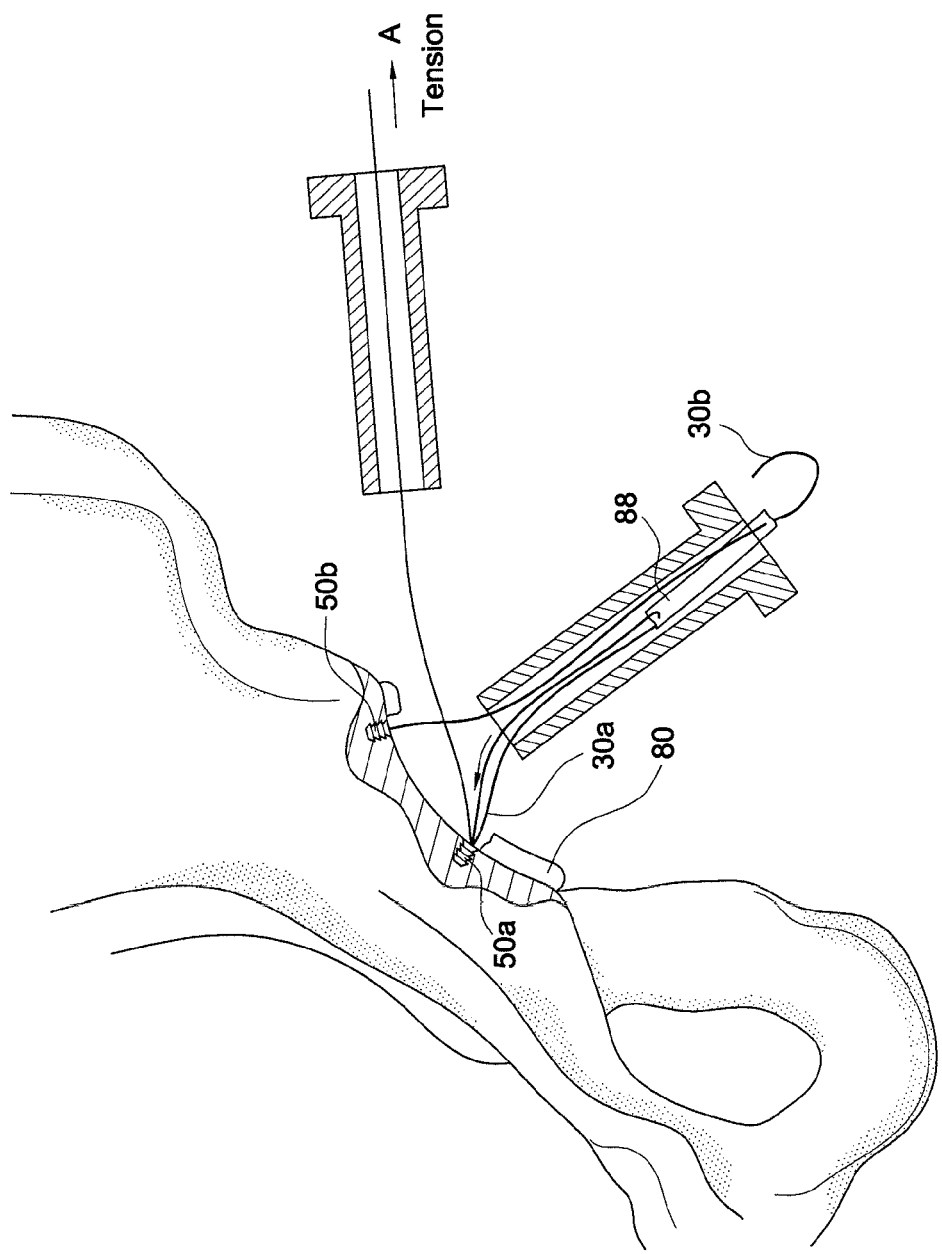

Technique for Hip Labral Reconstruction Using Multiple Knotless Anchors 50*a*, 50*b* (similar to knotless anchor 50)
   a. Insert Anchor 1 (anchor 50*a*) into bone at first edge 82*a* of segmental labral loss 82 of labrum 80 (FIG. 18)
   b. Insert Anchor 2 (anchor 50*b*) into bone 90 at second edge 82*b* of segmental labral loss 82 of labrum 80 (FIG. 18)
   c. Pass suture 30*a* from Anchor 1 (anchor 50*a*) through first end of labral graft 88 (FIG. 18)
   d. Pass suture 30*b* from Anchor 2 (anchor 50*b*) through second end of labral graft 88 (FIG. 18)
   e. Feed end of suture 30*a* from Anchor 1 (anchor 50*a*) back through cannula 70 and through the loop 44*a* of suture shuttle 40*a* of Anchor 1 (anchor 50*a*) (FIG. 18)
   f. Continue to pass end of suture 30*a* through the accessory portal (FIG. 19)
   g. Apply tension to end of suture through the accessory portal to parachute graft 88 into placement (FIGS. 19 and 20)
   h. Feed end of suture 30*b* from Anchor 2 (anchor 50*b*) through loop 44*b* of suture shuttle 40*b* and up through accessory portal; apply tension through accessory portal in the direction of arrow A (FIG. 19) to "parachute" graft 88 into the joint
   i. Apply tension to end of suture to complete placement of graft 88 (FIG. 20)
   j. Tension both ends of suture 30*a*, 30*b* to desired tension; tension posterior anchor 50*b* for completing anterior and posterior fixation (FIG. 20)
   k. Cut suture ends when repair completed (FIG. 21)
   l. Place additional anchors as needed (for example, anchors 50*c*, 50*d*) between the ends of the graft 88 to achieve fixation of the middle segment and complete graft fixation (FIG. 21)

FIGS. 22-25

Figure 22:
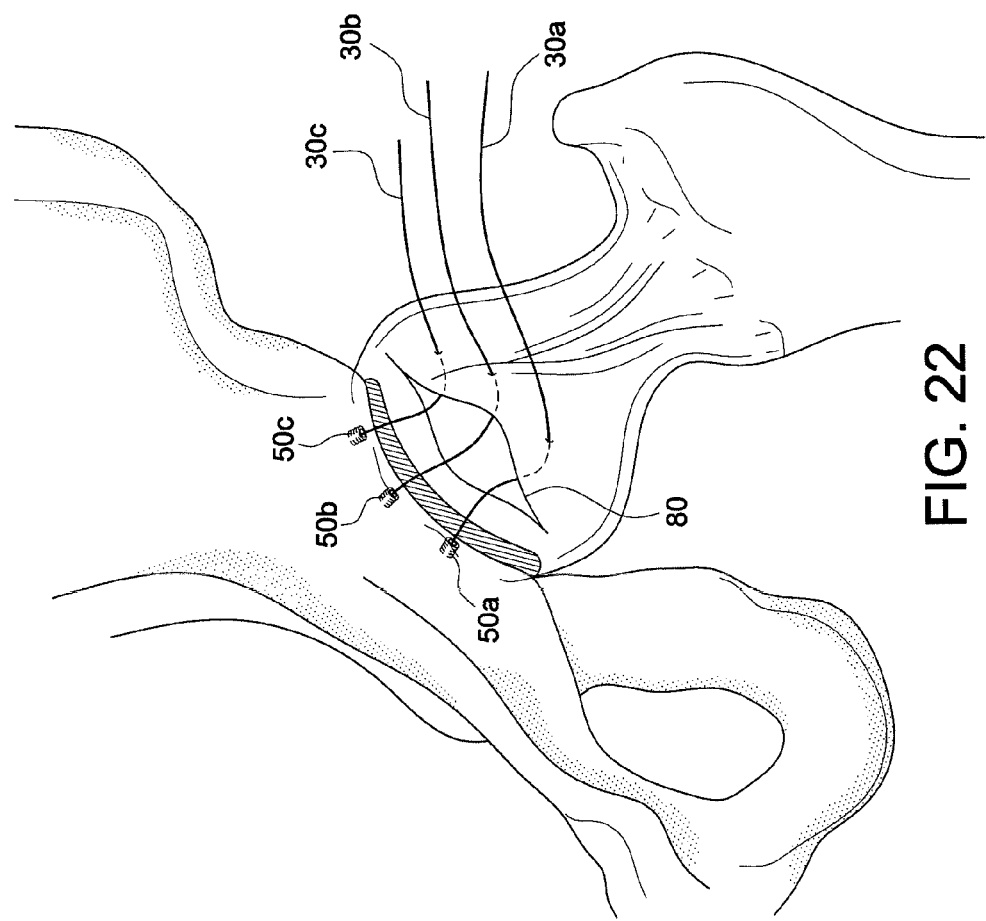
Figure 23:
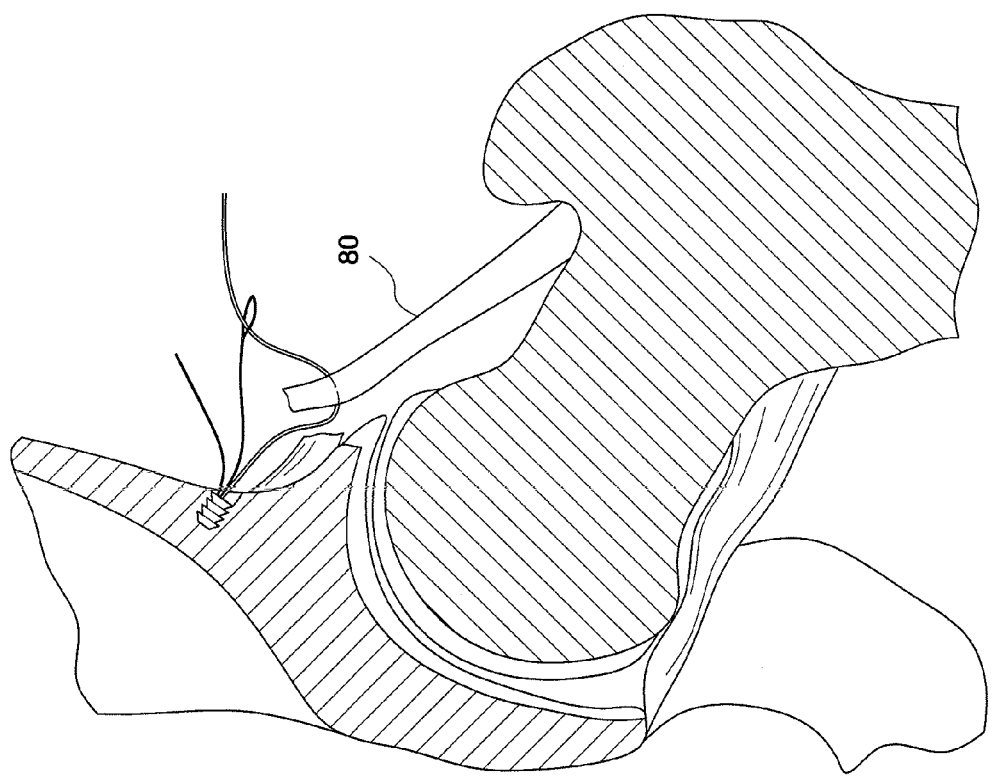

Technique for Hip Capsular Repair or Plication
   a. Place anchors 50*a*, 50*b*, 50*c*, 50*d* in bone 90 along tear; once anchors 50*a*, 50*b*, 50*c*, 50*d* are placed, the sutures 30*a*, 30*b*, 30*c*, 30*d* are passed through capsule 80 with a suture passing instrument (such as Bird Beak or Lasso suture passer) (FIG. 22 shows only three anchors)
   b. Using a suture passing instrument (not shown), pass suture 30*a*, 30*b*, 30*c* from each anchor 50*a*, 50*b*, 50*c* through capsule 80 (FIG. 22)
   c. Feed each end of suture 30*a*, 30*b*, 30*c*, 30*d* through suture shuttle 44*a*, 44*b*, 44*c*, 44*d* of respective anchor 50*a*, 50*b*, 50*c*, 50*d*
   d. Sequentially tension from medial to lateral each suture 30*a*, 30*b*, 30*c*, 30*d* to the desired tension; sutures are shuttled through anchors and sequentially tensioned medial to lateral (FIG. 24)
   e. Cut suture ends when repair complete (FIG. 25)

FIGS. 26-32

2) Simple Stitch—Single Anchor with Pass Suture Around Tissue and Attached to Bone
   a. Insert anchor 50 into bone 90 using driver, remove driver exposing suture 30 and suture shuttle 40 with wire loop 44 (of the shuttle/pull device 40) (FIG. 26)
      i. Can pre-drill bone hole or tap
   b. Pass suture 30 around tissue 80 using a suture passing instrument (FIG. 27)
   c. Feed suture 30 through loop 44 of suture shuttle 40 (FIG. 27)
   d. Pull end of suture shuttle 40 to pull suture 30 through itself and the anchor body (FIGS. 28-30)
   e. Pull suture 30 until desired tension and tissue position is reached (FIG. 31)
   f. Cut suture 30 when repair is complete (FIG. 32)

FIGS. 33-39

Figure 33:
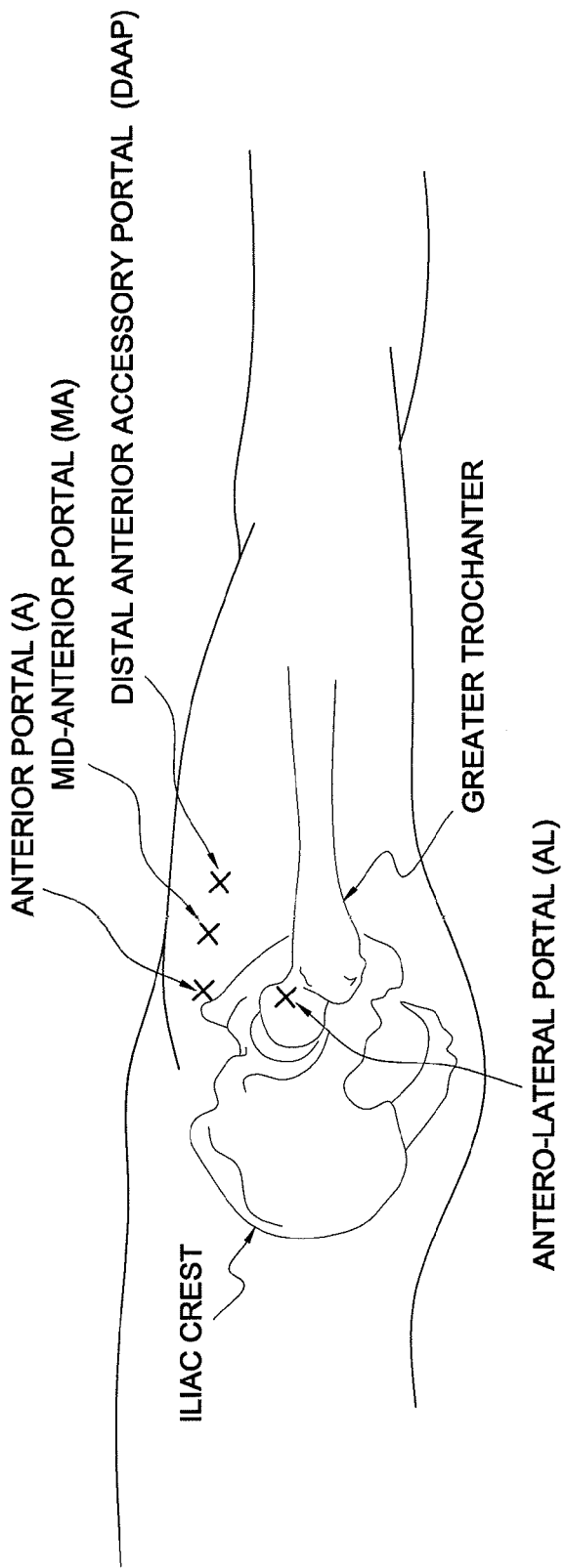
FIGS. 33-39 illustrate subsequent steps of a method of tissue repair (hip labral repair) using multiple tensionable knotless anchors according to an exemplary embodiment of the present invention.
Figure 35:
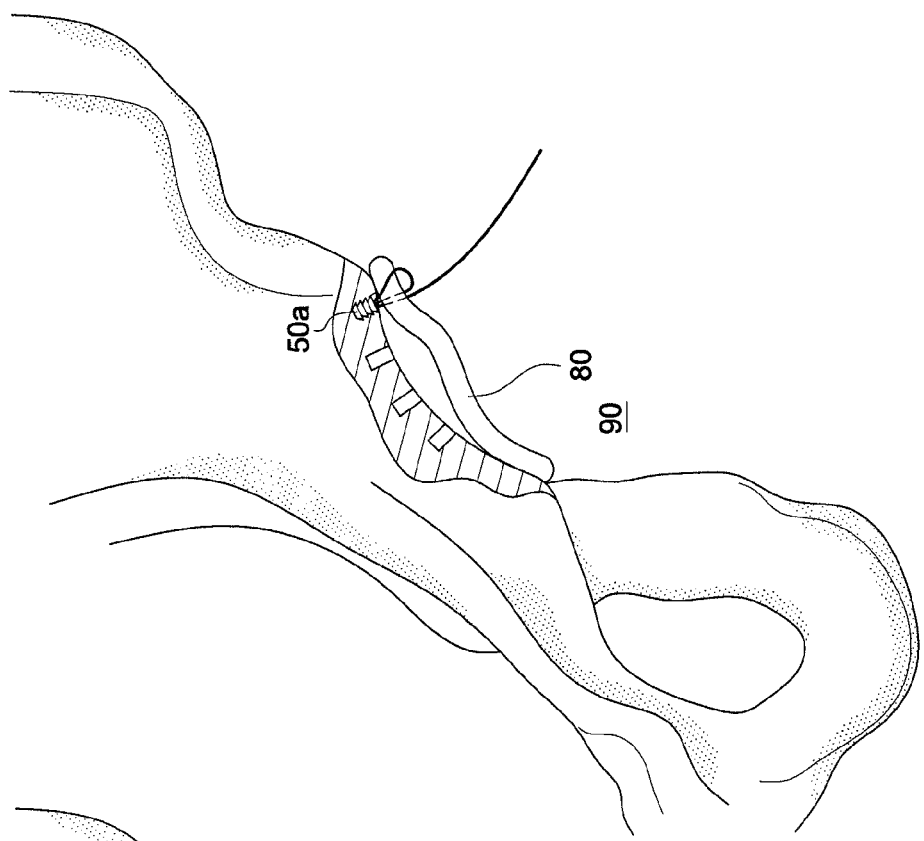
Figure 34:
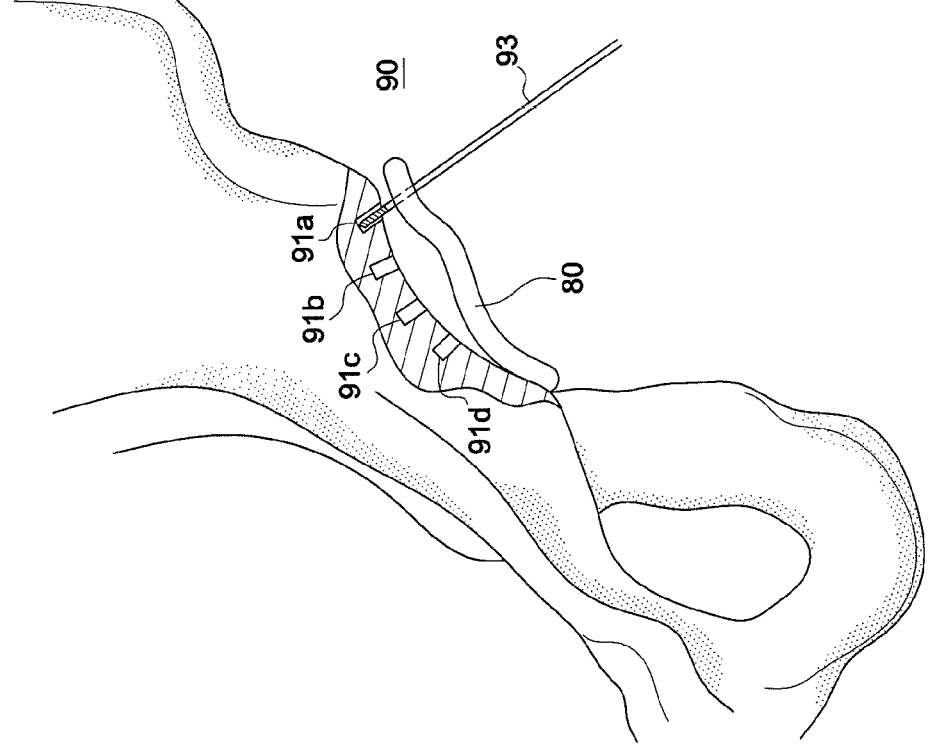
Figure 37:
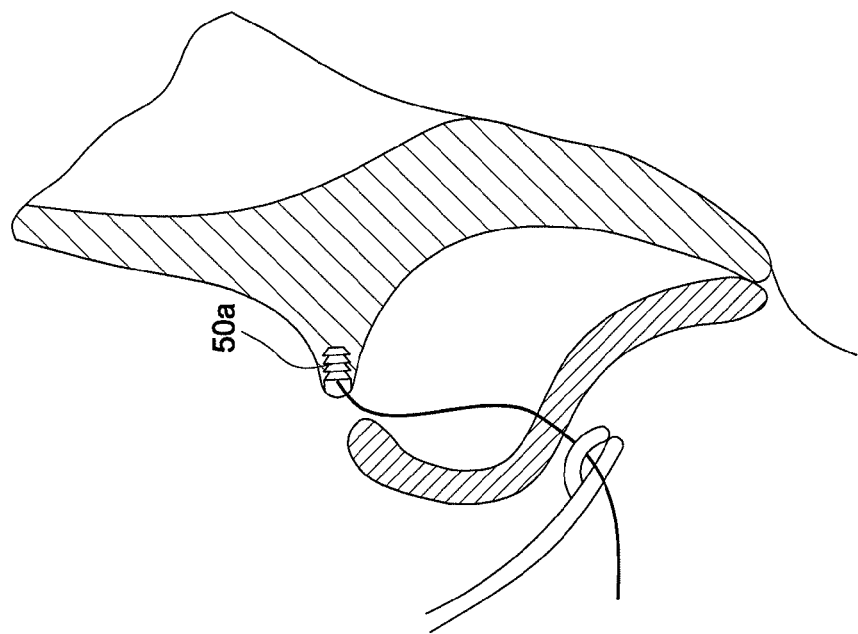
Figure 36:
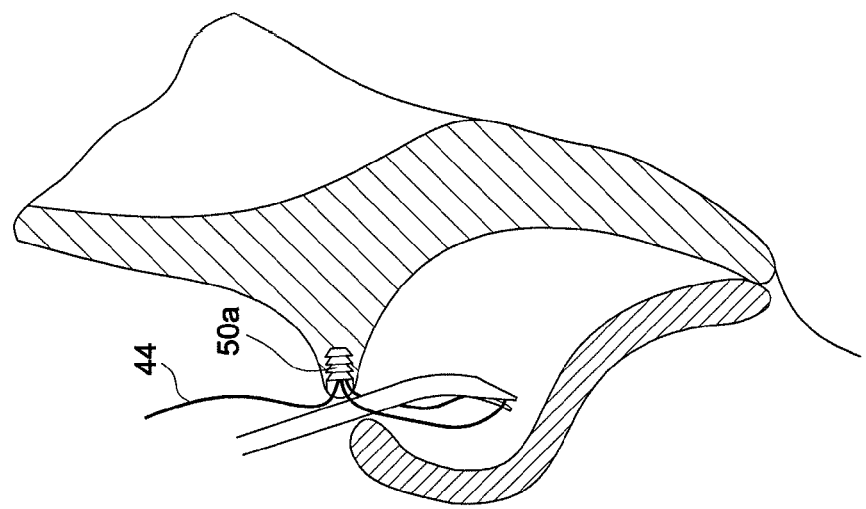
Figure 39:
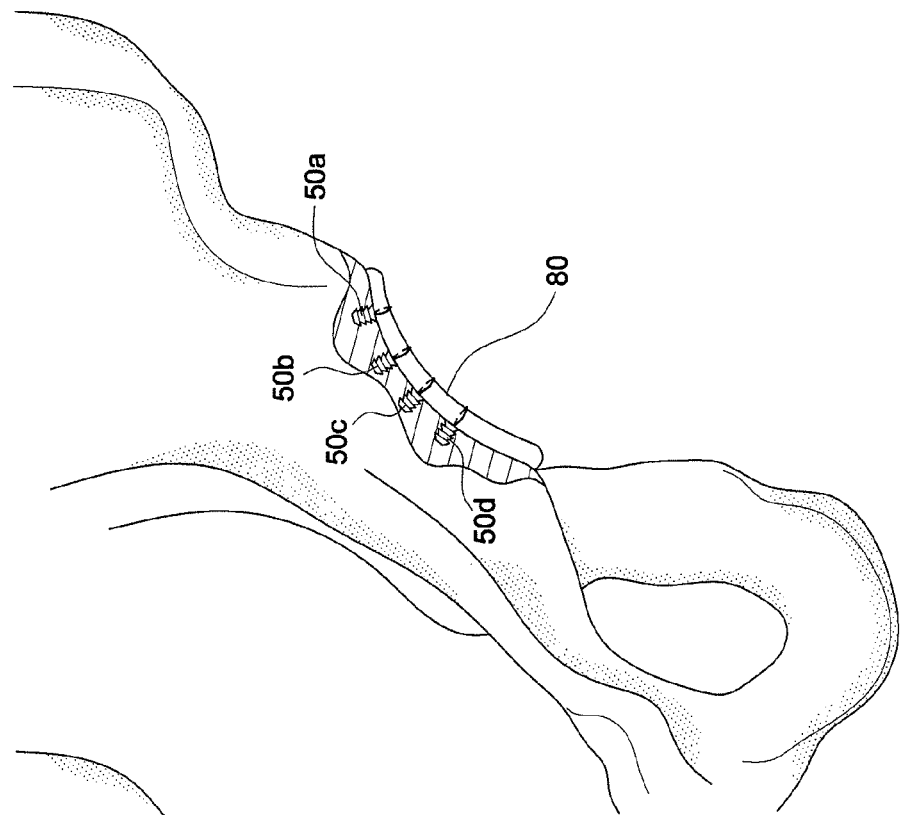
Figure 38:
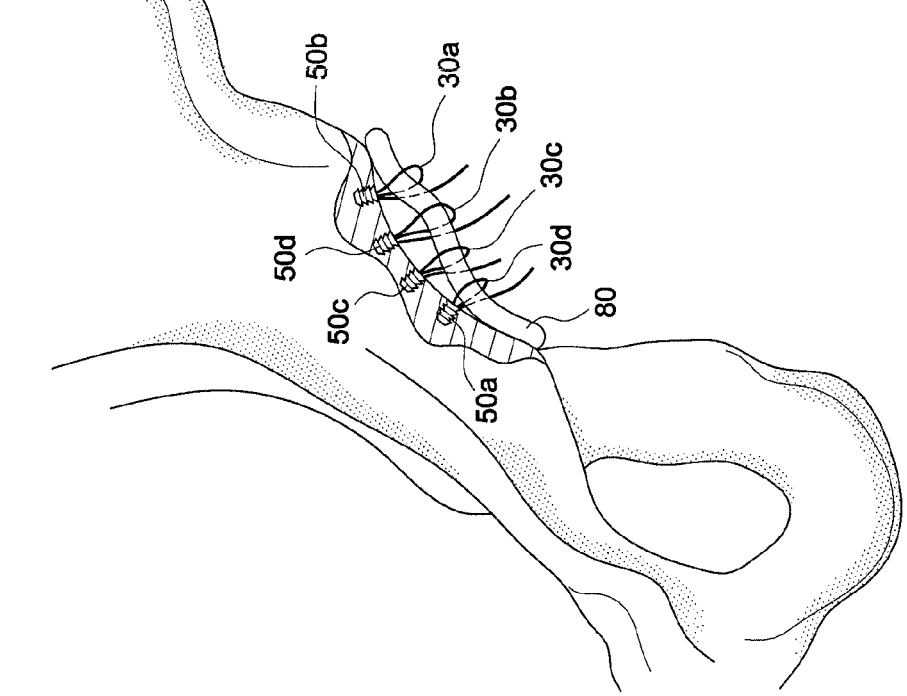

Technique for Hip Labral Repair (looped stitch)
   a. Drill all anchor holes 91*a*, 91*b*, 91*c*, 91*d* with drill 93 into hip 90 through Mid-Anterior Portal (MA) or Distal Anterior Accessory Portal (DAAP) or may drill one hole at a time (FIGS. 33 and 34); can use a 2-portal technique (antero-lateral portal (AL) and mid-anterior portal (MA)) or a 3-portal technique (antero-lateral portal (AL), distal-anterior accessory portal (DAAP) and anterior portal (A))
   b. Place first anchor 50*a* (FIG. 35), pass suture 30*a* behind labrum 80 (FIG. 36), retrieve suture 30*a* on front side of labrum 80 using suture passing instrument (FIG. 37)
   c. Feed end of suture 30*a* through loop 44*a* of suture shuttle 40*a* on anchor 50*a* (FIG. 37)
   d. Pull end of shuttle 40*a* (nitinol shuttle) to pass suture 30*a* through itself and anchor 50*a* and form splice within the anchor (FIG. 37)
   e. Place each subsequent anchor 50*b*, 50*c*, 50*d*, pass sutures 30*b*, 30*c*, 30*d* same as steps b-d
   f. Can store suture tails through a portal (for example, anterior portal) or outside of cannula (FIG. 38)
   g. Tension sutures to achieve desired placement and tension of labrum 80 (FIG. 39)

FIGS. 40-48

Figure 41:
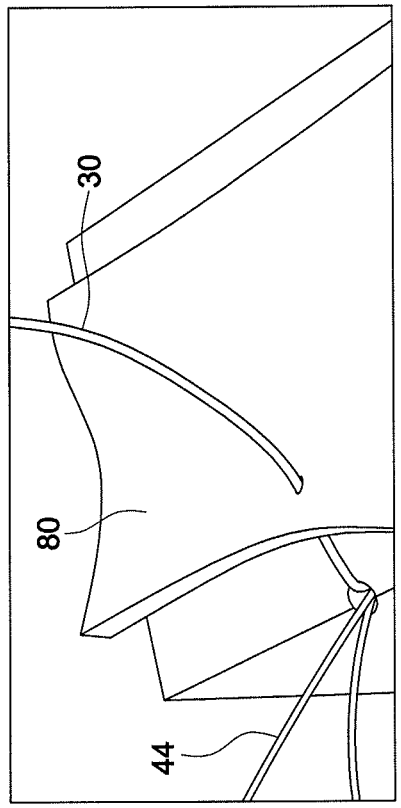
FIGS. 40-48 illustrate subsequent steps of a method of tissue repair (mattress stitch repair) using a tensionable knotless anchor according to an exemplary embodiment of the present invention.
Figure 43:
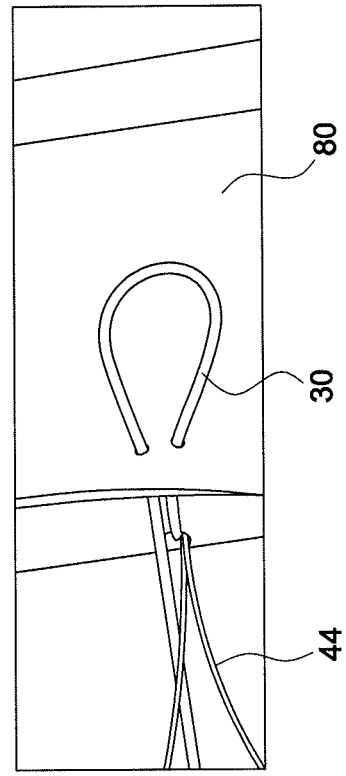
Figure 40:
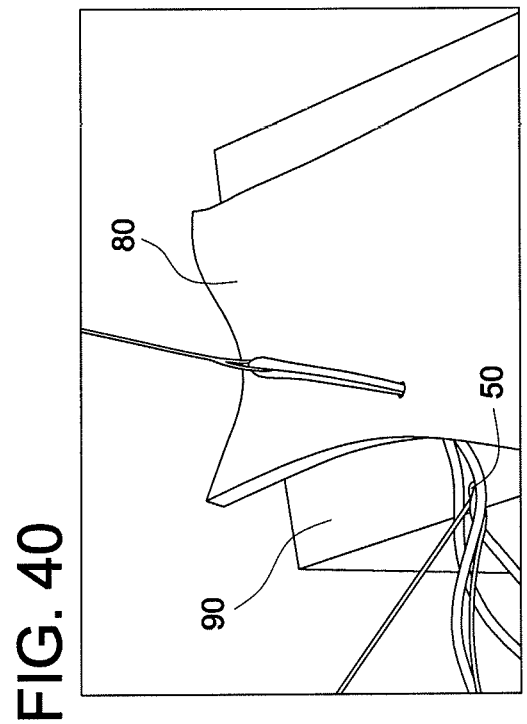
Figure 42:
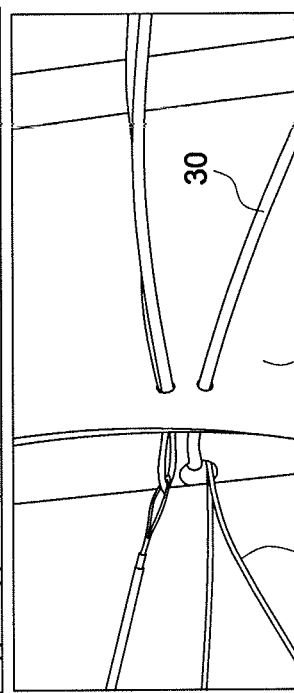
Figure 45:
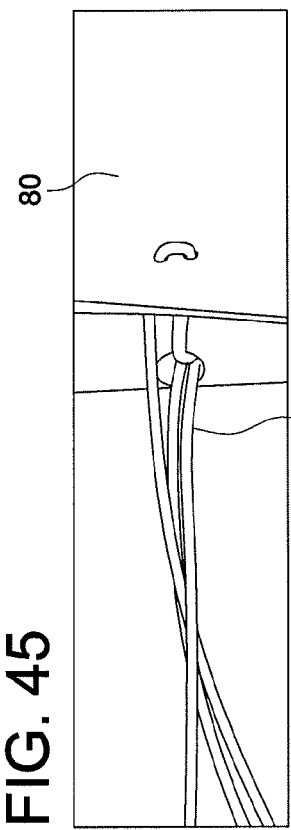
Figure 44:
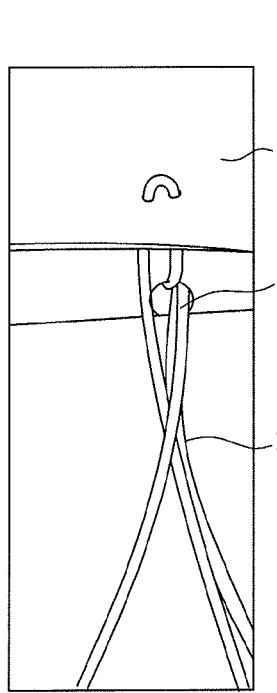
Figure 48:
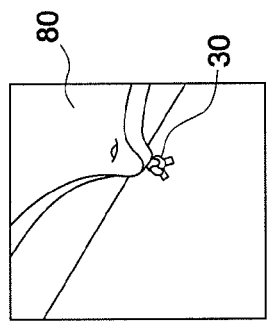
Figure 47:
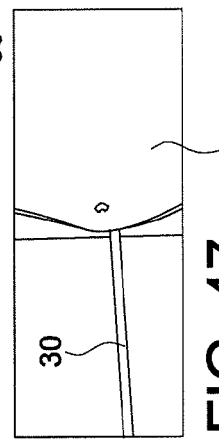
Figure 46:
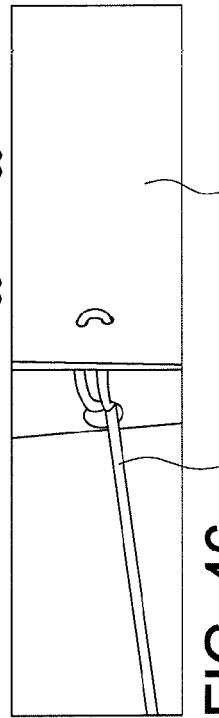

3) Mattress Stitch-Using Single Anchor to Attach Tissue
   a. Insert anchor 50 into bone 90 using driver, remove driver exposing suture 30 and suture passing construct 44 (wire loop 44 of shuttle 40) (FIG. 40)

i. Can pre-drill bone hole or tap
ii. Can go under tissue directly into bone
b. Using suture passing instrument, pass suture 30 up through the tissue 80 and back down through the tissue 80 (FIGS. 41-43)
c. Feed suture 30 through the suture shuttle 44 (FIG. 44)
d. Pull end of suture shuttle 44 to pull suture through itself and through the anchor body (FIGS. 45 and 46)
e. Continue to pull suture 30 until the tissue 80 is in desired position and tension (FIG. 47)
f. Cut suture 30 when repair is complete (FIG. 48)

FIGS. 49-51

Figure 49:
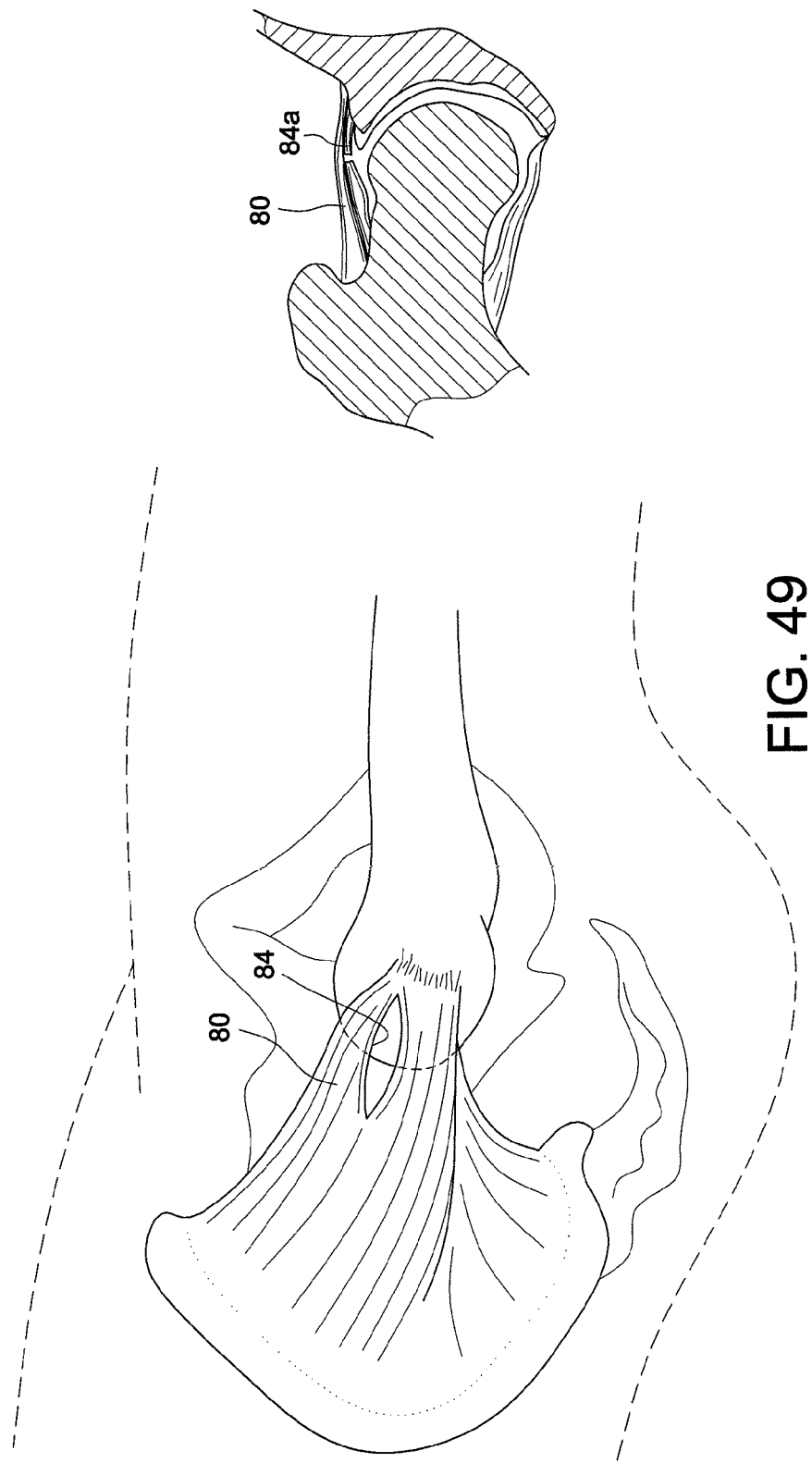
FIGS. 49-51 illustrate subsequent steps of a method of tissue repair (hip gluteus medius repair) using a tensionable knotless anchor according to an exemplary embodiment of the present invention.
Figure 50:
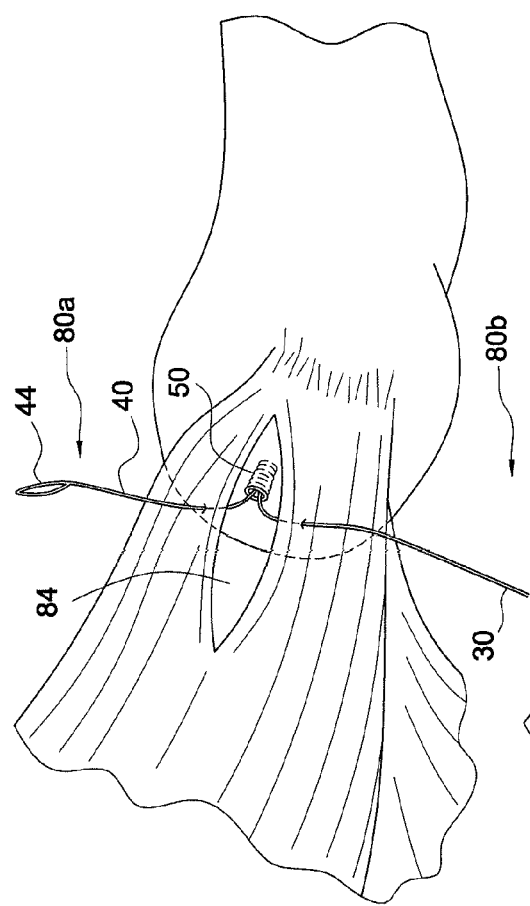
Figure 51:

Technique for Hip Gluteus Medius Repair-Transtendinous a. Create longitudinal incision 84 in tendon 80, allows access to deep-sided tear 84*a* (FIG. 49)
b. Place anchor 50 through incision 84 (FIG. 50)
c. Pass anchor suture shuttle 40 with loop/eyelet 44 through anterior side 80*a* of tendon 80 (FIG. 50)
d. Pass suture 30 through posterior side 80*b* of tendon 80 (FIG. 50)
e. Feed end of suture 30 through loop 44 of suture shuttle 40 (FIG. 51)
f. Pull suture shuttle 40 to pass suture 30 through itself and the anchor body to complete horizontal mattress
g. Tension suture end in direction of arrow A until desired tension (FIG. 51)
h. Cut end of suture 30 when repair completed
i. May use additional anchors depending on the size of the tear FIGS. 52 and 53

4) Modified Anchor Rotator Cuff Repair a. Anchor 150 is modified to have 2 sutures 30*a*, 30*b* loaded each with a suture shuttle 40*a*, 40*b* (with eyelets 44*a*, 44*b*) within a single anchor body; anchor 150 is similar in part to anchor 50 (a knotless SutureTak anchor) except for the fact that the post is optional and the anchor contains two or more sutures and suture shuttling devices (suture/nitinol constructs)
b. Anchor 150 has no post, sutures 30*a*, 30*b* are knotted at base of anchor 150 in knot 39 (FIG. 52); FIG. 52 shows an exemplary modified anchor 150 which is provided with no post but with two suture/nitinol loop constructs built within the anchor
c. Suture shuttle is inserted through a portion of the suture so both ends of shuttle extend from top of anchor as well as one end of suture
d. Insert Anchor 150 into bone 90 (a single anchor 150 can be used to hold the rotator cuff 80 together)
e. Using suture passer instrument, pass suture A (suture 30*a*) up through tissue 80 on one side of tear 84*a* (FIG. 53)
f. Feed suture A (suture 30*a*) through loop 44*a* of suture shuttle 40*a*
g. Pull suture shuttle 40*a*, pulling suture A (suture 30*a*) through itself and anchor body to create a splice within the anchor body
h. Using suture passer instrument, pass suture B (suture 30*b*) up through tissue 80 on opposite side of tear 84*a*
i. Feed suture B (suture 30*b*) through loop 44*b* of suture shuttle 40*b*
j. Pull suture shuttle 40*b*, pulling suture B (suture 30*b*) through itself and anchor body to create a second splice within the anchor body
k. Tension ends of suture A and B (sutures 30*a* and 30*b*) until desired tension is reached
l. Suture ends 30*a*, 30*b* may be cut when repair is complete (FIG. 53)

Embodiment B—Multiple Interconnected Knotless Anchor Constructs

Methods of Using Multiple Knotless Anchors to Create a Construct

FIGS. 54-59

Figure 56:
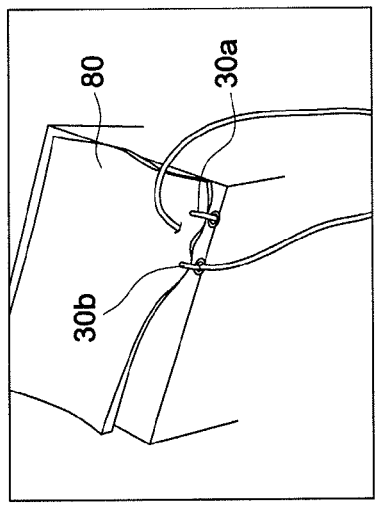
FIGS. 54-59 illustrate subsequent steps of a method of tissue repair (simple stitch with tied mattress repair) using multiple interconnected tensionable knotless anchors according to an exemplary embodiment of the present invention.
Figure 55:
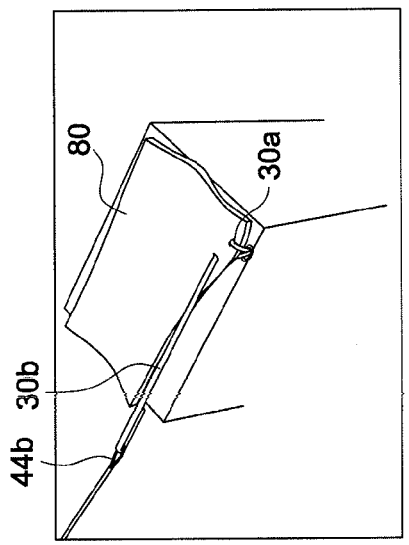
Figure 54:
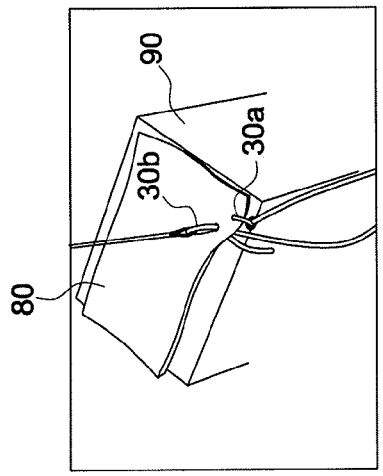
Figure 58:
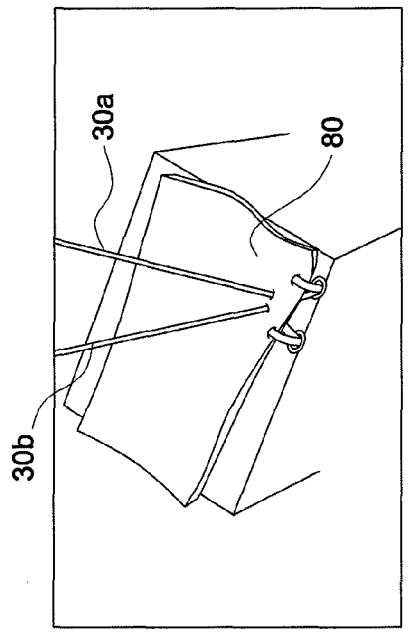
Figure 57:
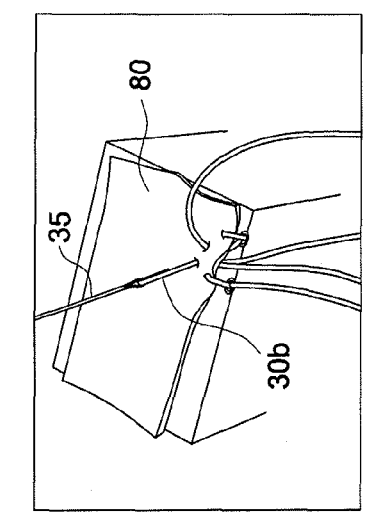
Figure 59:
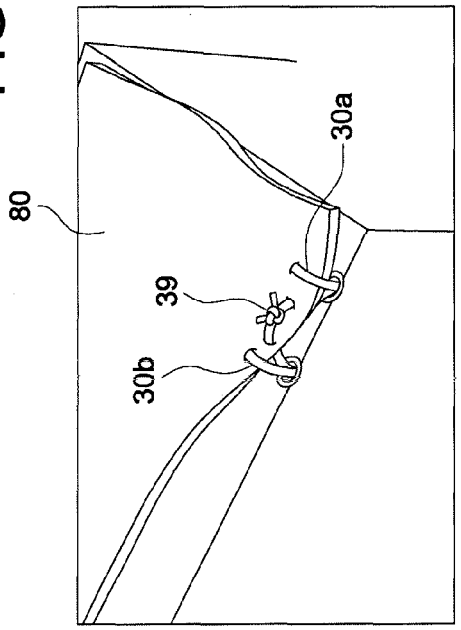

1) Simple Stitch with Tied Mattress a. Insert Anchor 1 (50*a*) into bone 90 using driver, remove driver exposing suture 30*a* and suture passing construct 40*a* with wire loop 44*a*
   i. Can pre-drill bone hole or tap
   ii. Can go through tissue or under it directly into bone
b. Using suture passing instrument, pass suture 30*a* through or around the tissue 80
c. Feed suture 30*a* through the loop 44*a* of suture shuttle 40*a*
d. Pull end of suture shuttle 40*a* to pull suture 30*a* through itself and through the anchor body to form inside splice (these are the same steps as Embodiment A1 steps a-d)
e. Pass the suture 30*a* back up through the tissue 80
f. Continue to pull suture 30*a* until the tissue is in desired position and tension
g. Insert Anchor 2 (50*b*) into desired position in bone 90, repeat steps b-f with suture 30*b* from Anchor 2 (50*b*)
h. Using suture passing instrument, pass suture 30*b* up through tissue 80 (FIG. 54)
i. Feed suture 30*b* through loop 44*b* of suture shuttle 40*b* (FIG. 55)
j. Pull end of suture shuttle 40*b* to pull suture 30*b* through itself and the anchor body to form another inside splice (FIG. 56)
k. Pass the suture 30*b* back up through the tissue 80 using suture passing instrument 35 (FIG. 57)
l. Pull ends of both sutures 30*a*, 30*b* until desired tension and tissue position is reached (FIG. 58)
m. Tie the suture limbs 30*a*, 30*b* of the two anchors 50*a*, 50*b* together in knot 39 to complete the mattress stitch (FIG. 59)
n. Cut the sutures 30*a*, 30*b* when repair is complete (FIG. 59)

FIGS. 60-71

Figure 69:
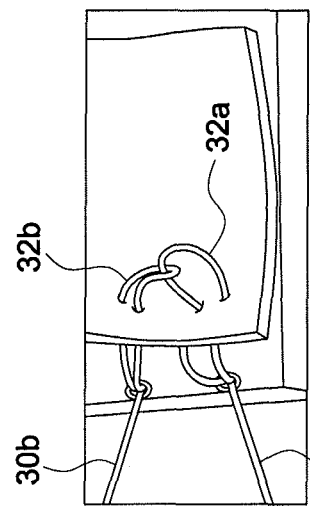
Figure 68:
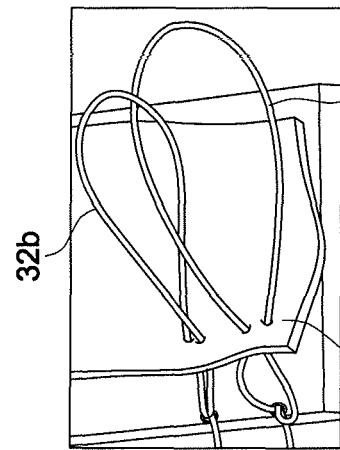
Figure 71:
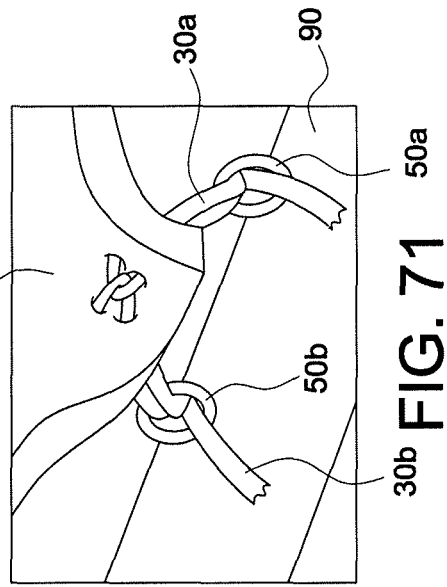
Figure 70:
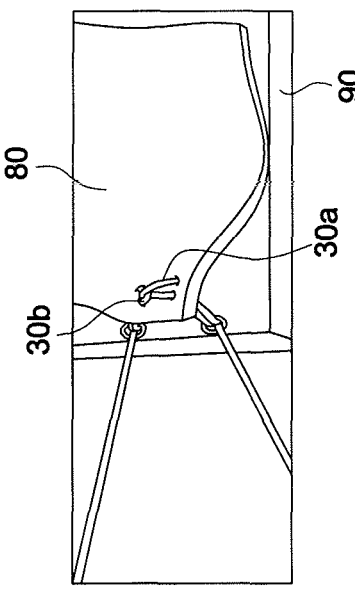

2) Interlocked Looped Mattress Over Two Anchors a. Insert Anchor 1 (50*a*) into bone 90 using driver, remove driver exposing suture 30*a* and suture passing construct 40*a* with wire loop 44*a*
   i. Can pre-drill bone hole or tap
   ii. Can go under tissue directly into bone
b. Using suture passing instrument 35, pass suture 30*a* up through the tissue 80 and back down through the tissue 80 (FIGS. 60 and 61)
c. Feed suture 30*a* through the loop 44*a* of suture shuttle 40*a* (FIG. 62)
d. Pull end of suture shuttle 40*a* to pull suture 30*a* through itself and through the anchor body to form splice within the anchor body
e. Continue to pull suture, leaving slack in loop 32*a* above the tissue 80 to pass the second suture 30*b* through it (FIG. 63)
f. Insert Anchor 2 (50*b*), remove driver, pass suture 30*b* from Anchor 2 (50*b*) up through tissue 80 using suture passing instrument 35 (FIG. 64)
g. Pass suture 30*b* through the suture loop 32*a* of Anchor 1 (50*a*) (FIG. 65)
h. Pass suture 30*b* back down through the tissue 80 (FIG. 66)

i. Feed end of suture 30*b* through loop 44*b* of the suture shuttle 40*b* of Anchor 2 (50*b*) (FIG. 67)

j. Pull end of suture shuttle 40*b* to pull suture 30*b* through itself and body of Anchor 2 (50*b*) to form another splice and leaving two interlocked loops 32*a*, 32*b* above the tissue 80 (FIG. 68)

k. Pull the two sutures 30*a*, 30*b* to the desired tension to complete the mattress stitch (FIGS. 69 and 70)

l. Cut the sutures 30*a*, 30*b* when the repair is complete (FIG. 71, also showing top view of the inserted anchors 50*a*, 50*b*)

FIGS. 72-75

3) Two or More Anchors in Daisy Chain a. Insert Anchor I (50*a*), insert Anchor II (50*b*), insert Anchor III (50*c*) all in bone 90, remove drivers (FIG. 72)

b. Using suture passing instrument, pass suture 30*a* of Anchor I (50*a*) up through the tissue 80 c. Feed the suture I (30*a*) through loop 44*b* of the suture shuttle 40*b* of Anchor II (50*b*)

d. Pass suture II (30*b*) of Anchor II (50*b*) up through tissue 80, feed through loop 44*c* of suture shuttle 40*c* of Anchor III (50*c*)

e. Pass the suture III (30*c*) up through tissue 80, feed through loop 44*a* of suture shuttle 40*a* of Anchor I (50*a*) (FIG. 73)

f. Pull suture shuttles 40*a*, 40*b*, 40*c* and respective sutures 30*a*, 30*b*, 30*c* through body of Anchors 50*a*, 50*b*, 50*c* (FIG. 74) to form respective splices within each of these anchors g. Tighten sutures 30*a*, 30*b*, 30*c* until desired tension (FIG. 75)

h. Cut all sutures 30*a*, 30*b*, 30*c* when repair completed i. Option: can be repeated with any number of anchors, in any order

FIGS. 76-95

Figure 78:
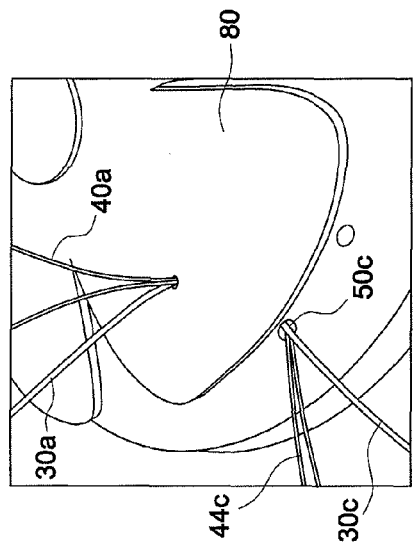
FIGS. 76-95 illustrate subsequent steps of a method of tissue repair (double row rotator cuff or Achilles tendon repair using daisy chain) using multiple interconnected tensionable knotless anchors according to an exemplary embodiment of the present invention.
Figure 77:
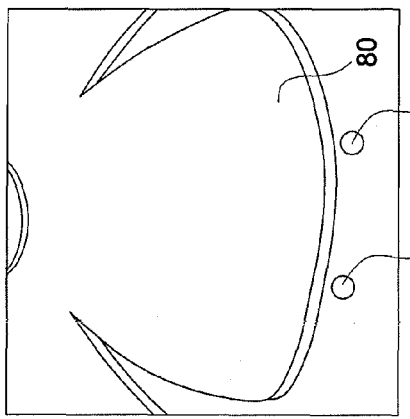
Figure 76:
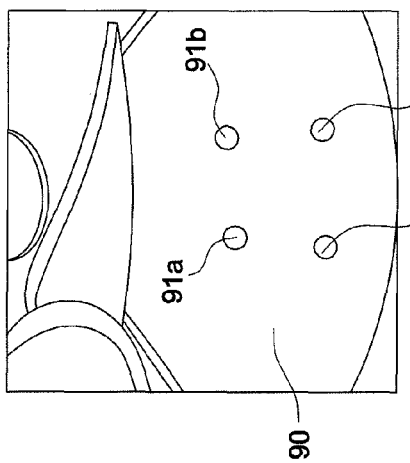
Figure 81:
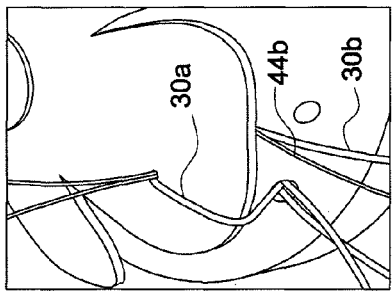
Figure 80:
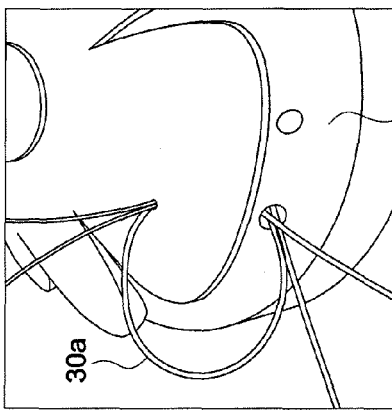
Figure 79:
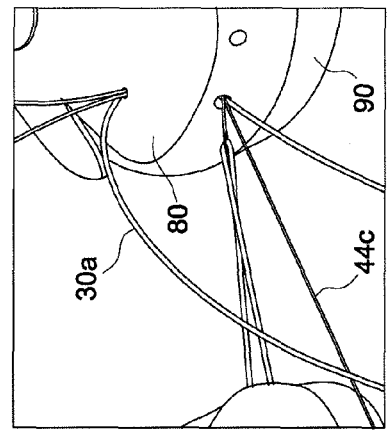
Figure 85:
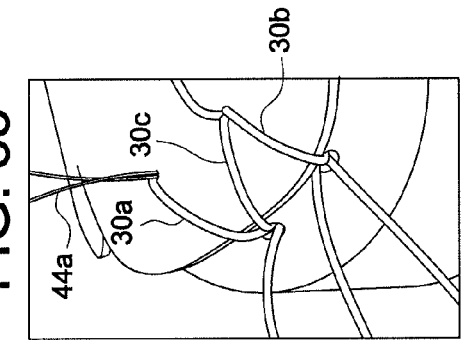
Figure 89:
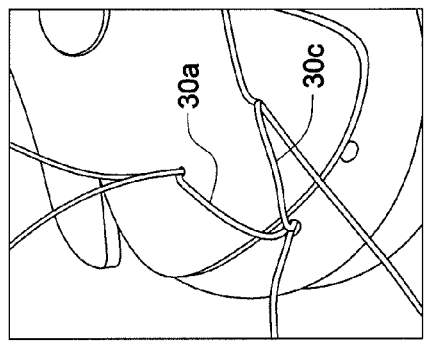
Figure 84:
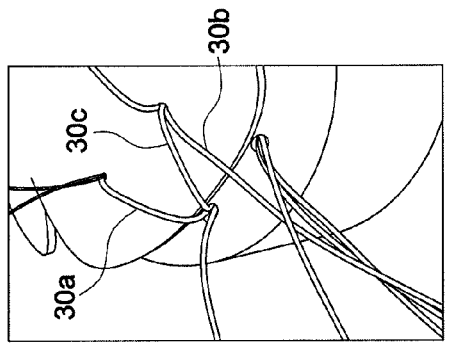
Figure 88:
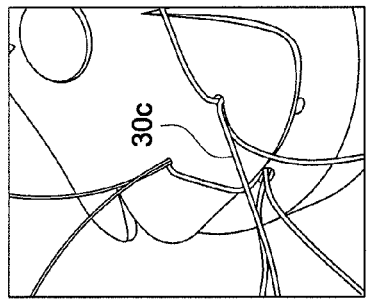
Figure 83:
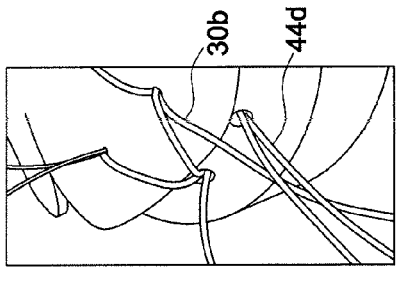
Figure 87:
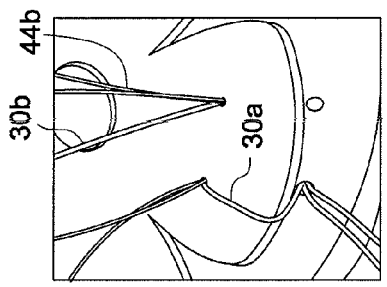
Figure 82:
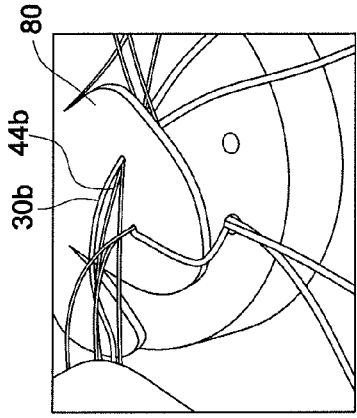
Figure 86:
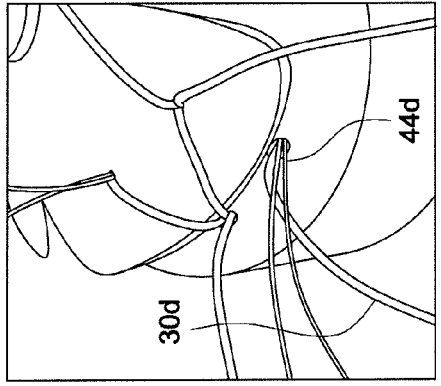
Figure 92:
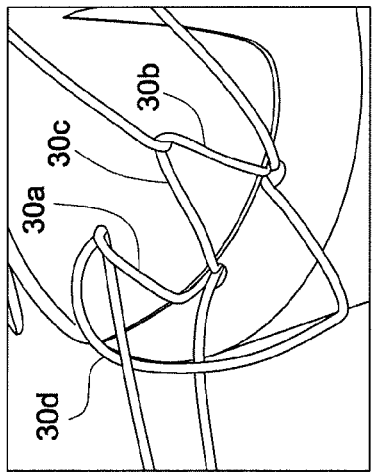
Figure 95:
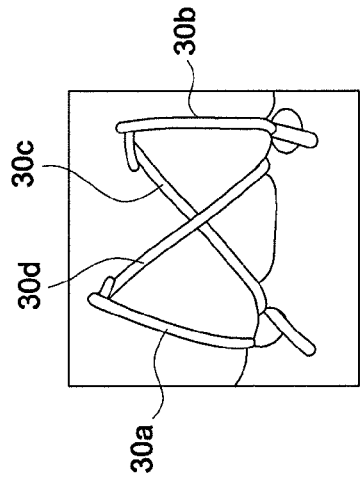
Figure 91:
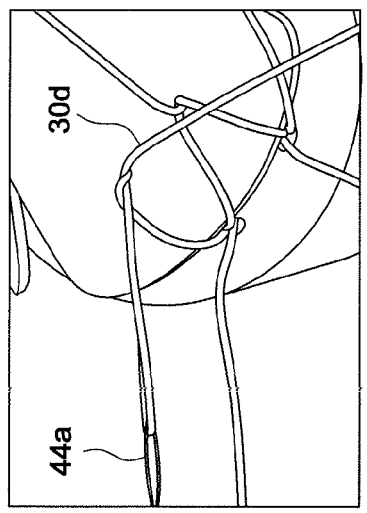
Figure 94:
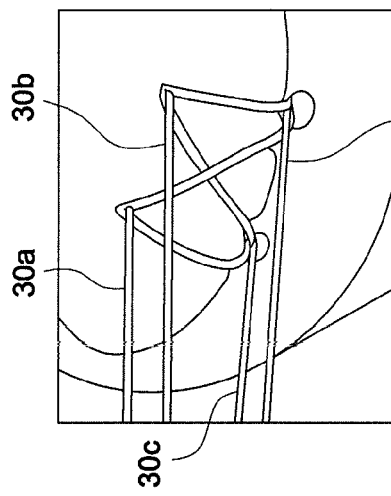
Figure 90:
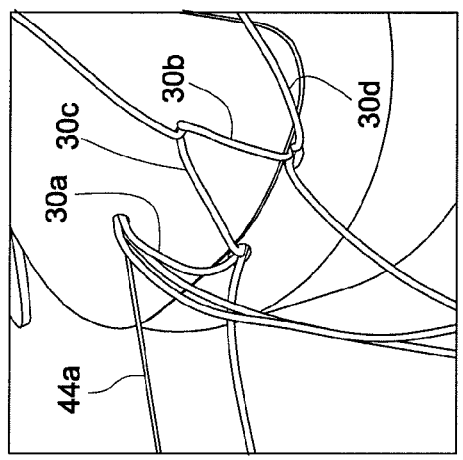
Figure 93:
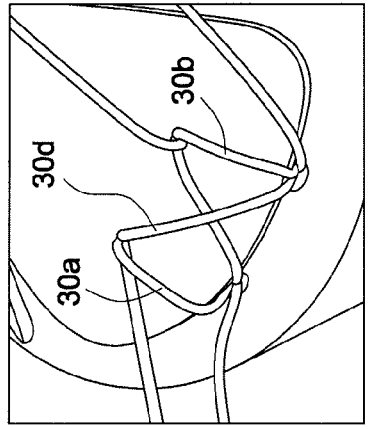

4) Double Row Rotator Cuff or Achilles Tendon Repair Using Daisy Chain a. Drill holes 91*a*, 91*b*, 91*c*, 91*d* for all 4 anchors 50*a*, 50*b*, 50*c*, 50*d*, two anchors under tissue 80 and two anchors on outside edge of tissue 80 (FIGS. 76 and 77)

b. Place Anchor I (50*a*) and Anchor III (50*c*), using suture passing instrument pass suture 30*a* and suture shuttle 40*a* with loop 44*a* from Anchor I (50*a*) up through tissue 80 (FIG. 78)

c. Feed end of suture I (30*a*) through loop 44*c* of suture shuttle 40*c* of Anchor III (50*c*) and shuttle suture through Anchor III (50*c*) (FIGS. 79 and 80)

d. Pull end of suture I (30*a*) until desired tension reached and insert Anchor II (50*b*) (FIG. 81)

e. Pass suture II (30*b*) and suture shuttle 40*b* with loop 44*b* up through tissue (FIGS. 82 and 83)

f. Feed end of suture III (30*c*) through loop 44*b* of suture shuttle 40*b* of Anchor II (50*b*) and shuttle suture III (30*c*) through Anchor II (50*b*) (FIG. 84)

g. Pull end of suture III (30*c*) until desired tension reached (FIG. 85)

h. Insert Anchor IV (50*d*) with suture 30*d* and shuttle loop 44*d* (FIG. 86)

i. Feed end of suture II (30*b*) through loop 44*d* of suture shuttle 40*d* of Anchor IV (50*d*) (FIG. 87)

j. Shuttle suture II (30*b*) through Anchor IV (50*d*) (FIG. 88)

k. Pull end of suture II (30*b*) until desired tension reached (FIG. 89)

l. Feed end of suture IV (30*d*) through loop 44*a* of suture shuttle 40*a* of Anchor I (50*a*) (FIG. 90)

m. Shuttle suture IV (30*d*) through Anchor I (50*a*) (FIG. 91)

n. Pull end of suture IV (30*d*) until desired tension reached (FIGS. 92 and 93)

o. Pull ends of sutures I, II, III, and IV (30*a*, 30*b*, 30*c*, 30*d*) to complete repair (FIG. 94)

p. Cut ends of sutures 30*a*, 30*b*, 30*c*, 30*d* (FIG. 95)

Embodiment C—Multiple Anchor Constructs Using 2 Different Types of Knotless Anchors Method of Using 2 Different Style Knotless Anchors Together

FIGS. 96-99

1) Two Anchor Mattress with Suture Shuttle (Anchor 1 is Anchor 50*a*, Anchor 2 is a Modified Anchor 250 in that it has No Suture, Only Suture Shuttle 40*b* with Loop 44*b*)

a. Insert Anchor 1 (50*a*) into bone 90 through or under tissue 80 and remove driver exposing suture 30*a* and loop 44*a* of suture shuttle 40*a* b. Insert Anchor 2 (250) into bone 90 and remove driver exposing suture shuttle 40*b* with loop 44*b* (FIG. 96)

c. Using suture passing instrument, pass the suture 30*a* from Anchor 1 (50*a*) up through the tissue 80 d. Using suture passing instrument, pass suture through tissue near site of Anchor 2 (250)

i. Optional: pass suture shuttle 40*b* of Anchor 2 (250) through tissue 80 near Anchor 2 (250)

e. Feed suture 30*a* through the loop 44*b* of suture shuttle 40*b* of Anchor 2 (250) (FIG. 97)

f. Pull end of suture shuttle 40*b* to pass suture 30*a* through the body of Anchor 2 (250) and form splice within the anchor body i. If used Optional d.i. step, then using shuttle 40*b*, pull suture 30*a* down through tissue 80, through Anchor 2 (250) body and back up through tissue 80, skip to step h g. Pass the suture 30*a* up through the tissue 80 near Anchor 2 (250)

h. Pass the suture 30*a* down through the tissue 80 near Anchor 1 (50*a*)

i. Feed the suture 30*a* through the loop 44*a* of suture shuttle 40*a* of Anchor 1 (50*a*) (FIG. 98)

j. Pull end 40*a* of the suture shuttle to pass suture 30*a* through itself and body of Anchor 1 (50*a*) and form splice within the anchor body (FIG. 99)

k. Pull the suture 30*a* until the desired placement of the tissue 80 and tension is reached l. Cut suture 30*a* to complete the repair (FIG. 99)

FIGS. 100 and 101

Options: Rotator Cuff Repair Using Two Anchor 2 (250) for Medial Row and Two Anchor 1 (50*a*) for the Lateral Row or Anchor 1 (50*a*) for Medial Row and Anchor 2 (250) for Lateral Row (FIG. 100)

FIG. 101

2) Modified Knotless Anchors in Double Row Construct a. Anchor 1 is modified to accommodate 2 sutures (1A & 1B) and 2 suture shuttles; anchor 1 is similar to anchor 150 of FIG. 52 b. Anchor 2 (350) is modified to accommodate 2 suture shuttles (2A & 2B) without any suture c. Insert Anchor 1 into bone for the lateral row d. Insert two Anchor 2 (350) into bone for the medial row e. Using suture passing instrument pass suture 1A from Anchor 1 through tissue near Anchor 2 f. Feed suture 1A through suture shuttle 2A of Anchor 2 g. Pull suture 1A through body of Anchor 2 and back up through tissue h. Feed suture 1A through suture shuttle 1A of Anchor 1 i. Pull suture shuttle 1A and suture 1A through itself and the body of Anchor 1
j. Pull until desired tension and tissue position obtained
k. Using suture passing instrument, pass suture 1B from Anchor 1 through tissue near $2^{nd}$ Anchor 2
l. Feed suture 1B through suture shuttle 2A of $2^{nd}$ Anchor 2
m. Pull suture 1B through body of $2^{nd}$ Anchor 2 and back up through tissue
n. Feed suture 1B through suture shuttle of Anchor 1
o. Pull suture shuttle and suture 1B through itself and body of Anchor 1
p. Pull suture 1B until desired tension and tissue position obtained
q. Insert $2^{nd}$ Anchor 1 into bone for the lateral row
r. Using suture passing instrument pass suture 1A of $2^{nd}$ Anchor 1 through tissue near Anchor 2
s. Feed suture 1A through suture shuttle 2B of Anchor 2
t. Pull suture 1A through body of Anchor 2 and back up through tissue
u. Feed suture 1A through suture shuttle 1A of $2^{nd}$ Anchor 1
v. Pull suture shuttle 1A and suture 1A through itself and body of $2^{nd}$ Anchor 1
w. Pull until desired tension and tissue position obtained
x. Using suture passing instrument, pass suture 1B from $2^{nd}$ Anchor 1 through tissue near $2^{nd}$ Anchor 2
y. Feed suture 1B through suture shuttle 2B of $2^{nd}$ Anchor 2
z. Pull suture 1B through body of $2^{nd}$ Anchor 2 and up through tissue
aa. Feed suture 1B through suture shuttle of $2^{nd}$ Anchor 1
bb. Pull suture shuttle and suture 1B through itself and body of $2^{nd}$ Anchor 1
cc. Pull suture 1B until desired tension and tissue position is obtained
dd. Cut all suture ends when repair is complete Options: Any Suture can be Loaded Through Any Anchor as Long as All Splices are Tightened.

The knotless suture constructs and systems of the present invention are used in conjunction with any knotless fixation devices which can allow a flexible strand and attached suture passing device to form a splice within the body of the fixation device. The fixation devices may be any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others.

The flexible strand 30 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Typically the suture will be UHMWPE suture without a core to permit ease of splicing. The shuttle/pull device may be a shuttle/pull suture device such as a FiberLink™ or a Nitinol loop.

The strands may also be formed of a stiff material, or combination of stiff and flexible materials, depending on the intended application. The strands may be also formed of suture tape or a combination of suture and tape, a stiff material, or combination of stiff and flexible materials, depending on the intended application. The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A method of tissue repair, comprising the steps of: installing at least one fixation device in bone, the fixation device comprising a body, a flexible strand extending through the body and a shuttling device threaded to the flexible strand within the fixation device through a splice region thereof, the flexible strand and the shuttling device being pre-loaded on the fixation device such that the entirety of the splice region of the flexible strand is located within the fixation device; passing the flexible strand through or around tissue to be fixated; pulling on the shuttling device to allow the flexible strand to form a splice through itself within the fixation device, and provide tensioning of the tissue to be fixated relative to the bone; and forming, with the flexible strand and the shuttling device, a knotless closed loop having an adjustable perimeter, after the steps of installing the fixation device in bone and passing the flexible strand through or around the tissue.

2. The method of claim 1, comprising the step of installing two or more fixation devices in the bone and passing a flexible strand from at least one of the two or more fixation devices around the tissue.

3. The method of claim 1, comprising the step of installing two or more fixation devices in the bone and passing a flexible strand from at least one of the two or more fixation devices through the tissue.

4. The method of claim 3, further comprising the step of forming a mattress stitch by passing a flexible strand from each of the plurality of fixation devices back and forth through the tissue.

5. The method of claim 3, further comprising the step of forming two knotless closed loops each having an adjustable perimeter.

6. The method of claim 5, wherein the two knotless closed loops are interlocked with each other.

7. The method of claim 1, wherein the tissue is soft tissue.

8. The method of claim 1, wherein the tissue is tendon, labrum, Achilles tendon, rotator cuff, biceps or capsular tissue.

9. The method of claim 1, further comprising the step of adjusting the length of the knotless closed loop to approximate tissue to bone.

10. The method of claim 1, further comprising the steps of:
installing the at least one fixation device into a hole in the bone; and
passing the flexible strand around or through the tissue to be fixated, and then through an eyelet of the shuttling device.

11. The method of claim 1, wherein the fixation device is an anchor with a post and a pair of openings symmetrically positioned relative to the post, the pair of openings extending in a direction about transversal to the longitudinal axis of the body, the pair of openings being configured to allow the flexible strand and attached shuttling device to be passed through the body of the fixation device and around the post.

12. The method of claim 1, wherein the flexible strand is a suture formed of ultrahigh molecular weight polyethylene and wherein the shuttling device is a suture passing instrument.

13. The method of claim 1, wherein the shuttling device is configured to be pulled out of the body of the fixation device.

14. A method of tissue repair, comprising the steps of: installing a plurality of fixation devices into bone, each of the fixation devices including a flexible construct extending through the fixation device, the flexible construct comprising a flexible strand and a corresponding shuttling device threaded to the flexible strand within the fixation device through a splice region thereof the flexible construct being pre-loaded on the fixation device such that the entirety of the splice region of the flexible strand is located within the fixation device; passing each of the flexible strands around or through tissue to be fixated, and then through an eyelet of the shuttling devices; and pulling on each of the shuttling devices to allow each of the flexible strands to form a splice through itself within the fixation device, and provide tensioning of the tissue to be fixated relative to the bone.

15. The method of claim 14, comprising the step of passing each of the flexible strands around or through tissue to be fixated, and then through its corresponding eyelet of the shuttling/pulling device.

16. The method of claim 14, comprising the step of passing each of the flexible strands around or through tissue to be fixated, and then through an eyelet of one of the corresponding shuttling devices of an adjacent fixation device.

17. The method of claim 16, wherein each of the flexible strands is passed through tissue to be fixated, and then through an eyelet of one of any other of the corresponding shuttling devices of any of the other fixation device of the plurality of fixation devices.

18. The method of claim 14, comprising the steps of:
installing a first, a second and a third fixation devices into bone, each of the first, second and third fixation devices including a flexible construct extending through each of the first, second and third fixation devices, the flexible construct comprising a flexible strand and a corresponding shuttling device attached to the flexible strand;
passing each of the flexible strands around or through tissue to be fixated;
passing the flexible strand of the first fixation device through an eyelet of the shuttling device of the second fixation device, passing the flexible strand of the second fixation device through an eyelet of the shuttling/pulling device of the third fixation device, and passing the flexible strand of the third fixation device through an eyelet of the shuttling/pulling device of the first fixation device; and
pulling on each of the shuttling devices to allow each of the flexible strands to form a splice through itself and within the fixation device, and provide tensioning of the tissue to be fixated relative to the bone.

19. The method of claim 18, wherein at least one of the first, second and third fixation devices is a knotless anchor.

20. A method of attaching tissue to bone using an anchor assembly including a driver and an anchor, the anchor comprising: an anchor body having a distal end, a proximal end, a longitudinal axis, and two surgical constructs pre-loaded within the anchor body, each of the two surgical constructs consisting of a suture and a suture passing instrument attached to the suture; the method comprising the steps of:
providing an anchor pre-loaded with two sutures by passing the sutures around a post of the anchor and extending the sutures within a cannulation of the anchor, the sutures being secured by a knot at a most distal end of the anchor;
securing the anchor pre-loaded with the sutures to a driver by tying the sutures to the driver;
threading two suture passing instruments through the sutures, each of the suture passing instruments being attached to one of the sutures;
installing the anchor, pre-loaded with the sutures and with the attached suture passing instruments, into the bone using the driver;
removing the driver;
passing the sutures around or through tissue to be fixated;
threading each of the sutures through a closed loop of each of their respective suture passing instruments;
pulling each of the suture passing instruments to allow each of the sutures to pass through itself, within the anchor body, and to form a splice in each of the sutures; and
removing the suture passing instruments and pulling on the sutures to approximate tissue to bone.

* * * * *